United States Patent
Bantia et al.

(10) Patent No.: US 9,492,452 B2
(45) Date of Patent: *Nov. 15, 2016

(54) METHODS AND COMPOSITIONS FOR INHIBITION OF POLYMERASE

(71) Applicant: BioCryst Pharmaceuticals, Inc., Durham, NC (US)

(72) Inventors: Shanta Bantia, Birmingham, AL (US); Pravin L. Kotian, Birmingham, AL (US); Yarlagadda S. Babu, Birmingham, AL (US)

(73) Assignee: BioCryst Pharmaceuticals, Inc., Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/531,471

(22) Filed: Nov. 3, 2014

(65) Prior Publication Data
US 2015/0051230 A1     Feb. 19, 2015

Related U.S. Application Data

(63) Continuation of application No. 13/879,110, filed as application No. PCT/US2011/056421 on Oct. 14, 2011.

(60) Provisional application No. 61/492,054, filed on Jun. 1, 2011, provisional application No. 61/393,522, filed on Oct. 15, 2010.

(51) Int. Cl.
| | |
|---|---|
| A61K 31/519 | (2006.01) |
| A61K 31/40 | (2006.01) |
| A61K 31/196 | (2006.01) |
| A61K 31/215 | (2006.01) |
| A61K 31/351 | (2006.01) |
| A61K 31/7064 | (2006.01) |
| A61K 45/06 | (2006.01) |
| C07H 7/06 | (2006.01) |
| C07D 487/04 | (2006.01) |

(52) U.S. Cl.
CPC ........... *A61K 31/519* (2013.01); *A61K 31/196* (2013.01); *A61K 31/215* (2013.01); *A61K 31/351* (2013.01); *A61K 31/7064* (2013.01); *A61K 45/06* (2013.01); *C07D 487/04* (2013.01); *C07H 7/06* (2013.01)

(58) Field of Classification Search
None
See application file for complete search history.

(56) References Cited

U.S. PATENT DOCUMENTS

| | | | |
|---|---|---|---|
| 5,985,848 A | 11/1999 | Furneaux et al. | |
| 7,560,434 B2* | 7/2009 | Babu et al. | 514/23 |
| 2009/0227637 A1* | 9/2009 | Weber et al. | 514/350 |
| 2010/0143300 A1 | 6/2010 | Babu et al. | |

FOREIGN PATENT DOCUMENTS

| | | |
|---|---|---|
| WO | WO-03/100009 A2 | 12/2003 |
| WO | WO-2012/063085 A2 | 5/2012 |
| WO | WO-2013/158746 A1 | 10/2013 |

OTHER PUBLICATIONS

Govorkova et al., Neuraminidase Inhibitor-Rimantadine Combinations Exert Additive and Synergistic Anti-Influenza Virus Effects in MDCK Cells, Antimicrobial Agents and Chemotherapy, 48(12):4855-4863, 2004.*
Extended European Search Report from EP 11833515.7 dated Mar. 19, 2014.
International Search Report and Written Opinion for corresponding PCT/US2011/056421 dated Feb. 13, 2012.
Eldrup, A. B., et al., "Structure-Activity Relationship of Heterobase-Modified 2'-C-Methyl Ribonucleosides as Inhibitors of Hepatitis C Virus RNA Replication," J. Med. Chem 2004, 47, pp. 5284-5297.
Australian Examination Report from AU 2011315902 dated Apr. 30, 2016.
Office Action from parent U.S. Appl. No. 13/879,110, dated Aug. 12, 2016.

* cited by examiner

*Primary Examiner* — Jeffrey S Lundgren
*Assistant Examiner* — Michael Schmitt
(74) *Attorney, Agent, or Firm* — Dana M. Gordon; Foley Hoag LLP

(57) ABSTRACT

The present invention is directed to methods and compositions for inhibition of viral nucleic acid polymerases, such as RNA and DNA polymerases, and methods and compositions that are useful for treating viral infections in subjects. The methods comprise administering to the subject a therapeutically effective amount of a compound of formula I, or a pharmaceutically acceptable salt or hydrate thereof, or a composition comprising a compound of formula I, or a pharmaceutically acceptable salt or hydrate thereof, and a pharmaceutically acceptable carrier. The composition or method may optionally comprise one or more additional anti-viral agents.

30 Claims, 14 Drawing Sheets

METHODS AND COMPOSITIONS FOR INHIBITION OF POLYMERASE

RELATED APPLICATIONS

This application is a continuation of U.S. patent application Ser. No. 13/879,110, filed Aug. 26, 2013; which claims the benefit of priority to Patent Cooperation Treaty Application number PCT/US11/056421, filed Oct. 14, 2011; which claims priority to U.S. Provisional Application No. 61/393,522, filed on Oct. 15, 2010; and U.S. Provisional Application No. 61/492,054, filed on Jun. 1, 2011.

This application claims priority to U.S. Provisional Application No. 61/393,522, filed on Oct. 15, 2010 and U.S. Provisional Application No. 61/492,054, filed on Jun. 1, 2011, both of which are incorporated herein by reference.

BACKGROUND

Viral diseases are responsible for both global pandemics and yearly seasonal epidemics such as influenza. Outbreaks may be characterized by potentiated virulence and may occur suddenly, resulting in serious mortalities. Importantly, viral diseases are not limited to humans. For example, influenza also affects livestock and birds, which may have significant impact on food supply in addition to increasing the risk of transmission to humans. Exemplary conditions related to viral infection include, for example, influenza, small pox, encephalitis, West Nile disease, yellow fever, Dengue fever, hepatitis, human immunodeficiency, polio, and Coxsackie.

The genome of the influenza A virus has an RNA-dependent RNA polymerase, which is a heterotrimeric complex of three subunits (PA, PB1 and PB2). The RNA polymerase catalyzes viral RNA transcription and replication. Because transcription and replication of the virus depends on the activity of RNA polymerase, this enzyme has become of interest as a target for development of new anti-viral compounds, especially in the wake of the recent emergence of drug resistant viruses.

SUMMARY OF THE INVENTION

The invention provides methods and compositions for inhibition of viral nucleic acid polymerases, and methods and compositions that are useful for treating, suppressing and/or preventing viral infections in subjects. The methods comprise administering to the subject a therapeutically effective amount of a compound of formula I, or a pharmaceutically acceptable salt or hydrate thereof, or a composition comprising a compound of formula I, or a pharmaceutically acceptable salt or hydrate thereof, and a pharmaceutically acceptable carrier. The composition or method may optionally comprise one or more additional anti-viral agents. The methods and compositions are useful for treating, suppressing and/or preventing viral infections in subjects that may arise from infection by one or more type of virus. Thus, the methods and compositions are useful for broad spectrum anti-viral treatment, suppression, and/or prevention.

The present invention is based, in part, on certain discoveries which are described more fully in the Examples section of the present application. For example, the present invention is based, in part, on the discovery that levels of viral titer in cells were markedly reduced upon treatment with a compound of formula I. Thus, the present invention also provides methods for reducing viral titer in a bodily fluid or cell comprising contacting said fluid or cell with a compound of formula I. The present invention is further based, in part, on the discovery that levels of viral titer in cells for several viruses were markedly reduced upon treatment with a compound of formula I, indicating broad spectrum antiviral activity for the compound of formula I against a variety of viral strains. Thus, the present invention also provides methods for reducing viral titer for several types, subtypes and/or strains of viruses in a bodily fluid or cell comprised of contacting said fluid or cell with a compound of formula I.

In some embodiments, the present invention provides a method for inhibiting a viral RNA or DNA polymerase comprising contacting the polymerase with an effective inhibitory amount of the compound of formula I, or a pharmaceutically acceptable salt, solvate, or hydrate thereof.

In some embodiments, the method is performed in vivo.

In some embodiments, the present invention provides a method for treating a subject suffering from an RNA viral infection which comprises administering to said subject a therapeutically effective amount of a compound of formula I, or pharmaceutically acceptable salt thereof.

In some embodiments, the bodily fluid is blood. In some embodiments, the bodily fluid is plasma. In some embodiments, the bodily fluid is blood serum.

In some embodiments, the subject is a mammal. In some embodiments the subject is a human. In some embodiments, the subject is avian. In some embodiments, the subject is a swine or pig.

These and other embodiments of the invention are further described in the following sections of the application, including the Detailed Description, Examples, and Claims.

Still other objects and advantages of the invention will become apparent to those of skill in the art from the disclosure herein, which is simply illustrative and not restrictive. Thus, other embodiments will be recognized by the skilled artisan without departing from the spirit and scope of the invention.

DETAILED DESCRIPTION

Figure 1:
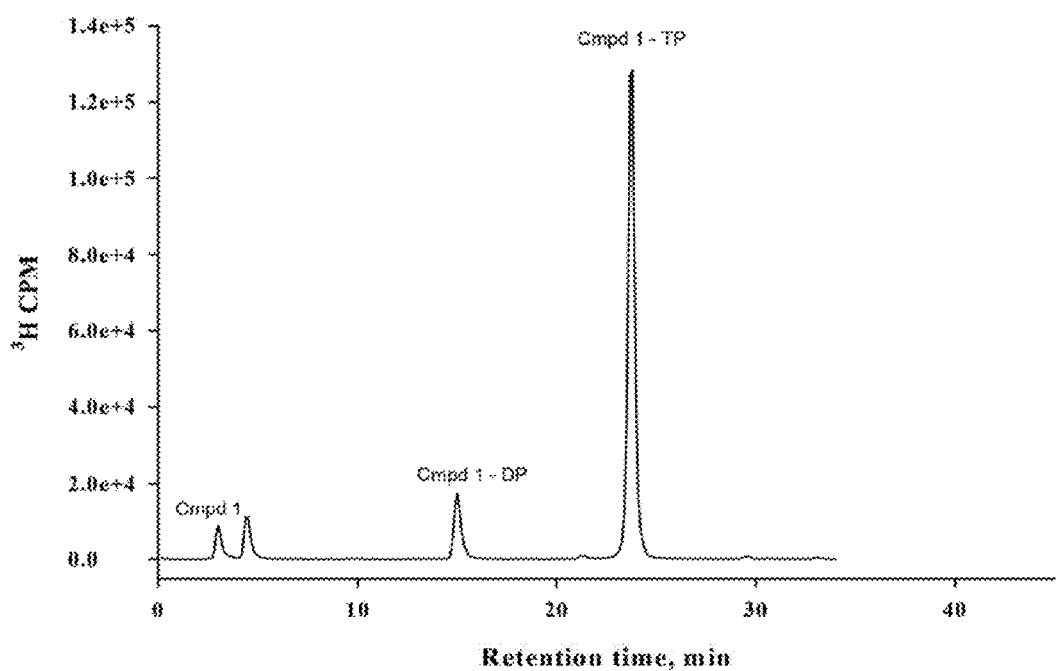
FIG. 1 shows the phosphorylation of compound 1 in human hepatocellular carcinoma (Huh-7) cells.

The invention provides methods and compositions for inhibition of viral nucleic acid polymerases, such as RNA and DNA polymerases, and methods and compositions that are useful for treating viral infections in subjects. The methods comprise administering to the subject a therapeutically effective amount of a compound of formula I, or a pharmaceutically acceptable salt or hydrate thereof, or a composition comprising a compound of formula I, or a pharmaceutically acceptable salt or hydrate thereof, and a pharmaceutically acceptable carrier. The composition or method may optionally comprise one or more additional anti-viral agents. The methods and compositions are useful for treating, suppressing and/or preventing viral infections in subjects that may arise from infection with one or more type of virus. Thus, the methods and compositions are useful for broad spectrum anti-viral treatment, suppression, and/or prevention.

In particular, the present invention relates to methods of treatment, suppression or and/or prevention of diseases or conditions relating to viral infection comprising administration of a compound of formula I, or pharmaceutically acceptable salt or hydrate thereof.

The compounds of formula (I) are as follows:

(I)

wherein A is OH or $NH_2$, and B is H or $NH_2$.

Thus, in some embodiments of the compound of formula (I), A is $NH_2$.

In some embodiments of the compound of formula (I), B is $NH_2$.

In some embodiments of the compound of formula (I), A is OH.

In yet some embodiments of the compound of formula (I), B is H.

In still some embodiments of the compound of formula (I), A is $NH_2$ and B is H.

In still some embodiments of the compound of formula (I), A is OH and B is $NH_2$.

In still some embodiments of the compound of formula (I), A is $NH_2$ and B is $NH_2$.

In still some embodiments of the compound of formula (I), A is OH and B is H.

The present invention is based, in part, on certain discoveries which are described more fully in the Examples section of the present application. For example, the present invention is based, in part, on the discovery that levels of viral titer in cells were markedly reduced upon treatment with a compound of formula I. Thus, in some embodiments, the present invention provides methods for reducing viral titer in a bodily fluid or cell comprised of contacting said fluid or cell with a compound of formula I. The present invention is further based, in part, on the discovery that levels of viral titer in cells for several viruses were markedly reduced upon treatment with a compound of formula I, thus indicating broad spectrum antiviral activity for the compound of formula I against a variety of viral strains. Thus, the present invention also provides methods for reducing viral titer for several types, subtypes and/or strains of viruses in a bodily fluid or cell comprised of contacting said fluid or cell with a compound of formula I.

The compounds of the present invention are prepared in different forms, such as salts, hydrates, solvates, or complexes, and the invention includes compositions and methods encompassing all variant forms of the compounds. In some embodiments, the compounds are prepared as hydrates of salts.

ABBREVIATIONS AND DEFINITIONS

The abbreviation "PNP" refers to purine nucleoside phosphorylase.

The term "compound(s) of the invention" as used herein means a compound of formula I, and may include salts, tautomeric forms, hydrates and/or solvates thereof. Compounds of formula I may also include solvates or hydrates of salts thereof.

The term "solvate" as used herein means a compound of formula I, or a pharmaceutically acceptable salt thereof, wherein molecules of a suitable solvent are incorporated in the crystal lattice. A suitable solvent is physiologically tolerable at the dosage administered. Examples of suitable solvents are ethanol, water and the like. When water is the solvent, the molecule is referred to as a "hydrate."

A "pharmaceutical composition" refers to a mixture of one or more of the compounds described herein, or pharmaceutically acceptable salts, or hydrates thereof, with other chemical components, such as physiologically acceptable carriers and excipients. The purpose of a pharmaceutical composition is to facilitate administration of a compound to an organism.

The term "pharmaceutically acceptable salt" is intended to include salts derived from inorganic or organic acids including, for example hydrochloric, hydrobromic, sulfuric, nitric, perchloric, phosphoric, formic, acetic, lactic, maleic, fumaric, succinic, tartaric, glycolic, salicylic, citric, methanesulfonic, benzenesulfonic, benzoic, malonic, trifluoroacetic, trichloroacetic, naphthalene-2 sulfonic and other acids. Pharmaceutically acceptable salt forms may also include forms wherein the ratio of molecules comprising the salt is not 1:1. For example, the salt may comprise more than one inorganic or organic acid molecule per molecule of base, such as two hydrochloric acid molecules per molecule of compound of formula (I). As another example, the salt may comprise less than one inorganic or organic acid molecule per molecule of base, such as two molecules of compound of formula (I) per molecule of tartaric acid. Salts may also exist as solvates or hydrates.

The term "acid" contemplates all pharmaceutically acceptable inorganic or organic acids. Inorganic acids include mineral acids such as hydrohalic acids, such as hydrobromic and hydrochloric acids, sulfuric acids, phosphoric acids and nitric acids. Organic acids include all pharmaceutically acceptable aliphatic, alicyclic and aromatic carboxylic acids, dicarboxylic acids, tricarboxylic acids, and fatty acids. Preferred acids are straight chain or branched, saturated or unsaturated C1-C20 aliphatic carboxylic acids, which are optionally substituted by halogen or by hydroxyl groups, or C6-C12 aromatic carboxylic acids. Examples of such acids are carbonic acid, formic acid, fumaric acid, acetic acid, propionic acid, isopropionic acid, valeric acid, alpha-hydroxy acids, such as glycolic acid and lactic acid, chloroacetic acid, benzoic acid, methane sulfonic acid, and salicylic acid. Examples of dicarboxylic acids include oxalic acid, malic acid, succinic acid, tataric acid and maleic acid. An example of a tricarboxylic acid is citric acid. Fatty acids include all pharmaceutically acceptable saturated or unsaturated aliphatic or aromatic carboxylic acids having 4 to 24 carbon atoms. Examples include butyric acid, isobutyric acid, sec-butyric acid, lauric acid, palmitic acid, stearic acid, oleic acid, linoleic acid, linolenic acid, and phenylsteric acid. Other acids include gluconic acid, glycoheptonic acid and lactobionic acid.

As used herein the term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent up or down (higher or lower).

An "effective amount", "sufficient amount" or "therapeutically effective amount" as used herein is an amount of a compound that is sufficient to effect beneficial or desired results, including clinical results. As such, the effective amount may be sufficient, for example, to reduce or ameliorate the severity and/or duration of the viral infection, or one or more symptoms thereof, prevent the advancement of the viral infection, prevent the recurrence, development, or onset of one or more symptoms associated with the viral infection, prevent or reduce the replication or multiplication of a virus, prevent or reduce the production and/or release of a viral particle, enhance or otherwise improve the prophylactic or therapeutic effect(s) of another therapy. An effective amount also includes the amount of the compound of formula I that avoids or substantially attenuates undesirable side effects.

As used herein and as well understood in the art, "treatment" is an approach for obtaining beneficial or desired results, including clinical results. Beneficial or desired clinical results may include, but are not limited to, alleviation or amelioration of one or more symptoms or conditions, diminution of extent of disease, a stabilized (i.e., not worsening) state of disease, preventing spread of disease, delay or slowing of disease progression, amelioration or palliation of the disease state and remission (whether partial or total), whether detectable or undetectable. "Treatment" can also mean prolonging survival as compared to expected survival if not receiving treatment.

The term "carrier" refers to a diluent, adjuvant, excipient, or vehicle with which a compound is administered. Non-limiting examples of such pharmaceutical carriers include liquids, such as water and oils, including those of petroleum, animal, vegetable or synthetic origin, such as peanut oil, soybean oil, mineral oil, sesame oil and the like. The pharmaceutical carriers may also be saline, gum acacia, gelatin, starch paste, talc, keratin, colloidal silica, urea, and the like. In addition, auxiliary, stabilizing, thickening, lubricating and coloring agents may be used. Other examples of suitable pharmaceutical carriers are described in "Remington's Pharmaceutical Sciences" by E. W. Martin; herein incorporated by reference in its entirety.

The terms "animal," "subject" and "patient" as used herein include all members of the animal kingdom including, but not limited to, mammals, animals (e.g., cats, dogs, horses, swine, etc.) and humans.

DESCRIPTION

The present invention provides methods and compositions for inhibition of viral nucleic acid polymerases, such as DNA and/or RNA viral polymerases, and methods and compositions that are useful for treating viral infections in subjects. The methods comprise administering to the subject a therapeutically effective amount of a compound of formula I, or a pharmaceutically acceptable salt thereof, or a composition comprising a compound of formula I, or a pharmaceutically acceptable salt or hydrate thereof, and a pharmaceutically acceptable carrier. The composition or method may optionally comprise one or more additional anti-viral agents. The methods and compositions are useful for treating, suppressing and/or preventing viral infections in subjects that may arise from infection by one or more family, genus, subtype, serotype, or strain of virus.

The compounds of formula I are 9-deazaadenine derivatives generally known as immucillins, the syntheses of which are described, for example, in WO 03/80620, and by Evans et al., in *Tetrahedron* 2000, 56, 3053 and *J. Org. Chem.* 2001, 66(17), 5723 (each of which herein incorporated by reference in its entirety). Syntheses of similar structures are discussed, for example, in U.S. Pat. Nos. 5,985,848; 6,066,722; 6,228,741 and PCT publications WO 2003/080620 and 2008/030119 (each of which herein incorporated by reference in its entirety). Immucillin derivatives have been studied as PNP inhibitors (See, Kicska et al., *J. Biol. Chem.* 2002, 277, 3219-3225, and Kicska et al., *J. Biol. Chem.* 2002, 277, 3226-3231; each of which herein incorporated by reference in its entirety). Some immucillins have also been studied as 5'-methylthioadenosine phosphorylase (MTAP) or 5'-methylthioadenosine nucleosidase (MTAN) inhibitors. Such mechanisms have been implicated in the treatment of cancer and bacterial infections (See, WO 03/080620, herein incorporated by reference in its entirety).

The compounds of formula I may exhibit tautomeric properties. Thus, the present invention also encompasses tautomeric forms of compounds of formula I, and mixtures thereof. It will further be appreciated that some compounds exist as pharmaceutically acceptable salts, solvates, and/or hydrates, each of which are also within the embodiments of the invention.

In some embodiments, the compound of formula I exists as a pharmaceutically acceptable salt. In some embodiments, the salt form is about a 1:1 ratio of acid and compound of formula I. In some embodiments, the salt form is greater than about a 1:1 ratio of acid and compound of formula I. In some embodiments, the salt form is about a 2:1 ratio of acid and compound of formula I. In some embodiments, the salt form exists as a hydrate.

In some embodiments, the compound of formula I exists as a hydrate or solvate.

The compounds of the disclosure therefore are useful in treating and/or preventing viral infections in a host or subject. The methods of the invention may be used in treating and/or preventing disease states or conditions caused by and/or related to such viral infections. Examples of such viral infections include, but are not limited to, adenovirus, rhinovirus, hepatitis, immunodeficiency virus, polio, measles, Ebola, Coxsackie, Rhino, West Nile, small pox, encephalitis, yellow fever, Dengue fever, influenza (including human, avian, and swine), lassa, lymphocytic choriomeningitis, junin, machuppo, guanarito, hantavirus, Rift Valley Fever, La Crosse, California encephalitis, Crimean-Congo, Marburg, Japanese Encephalitis, Kyasanur Forest, Venezuelan equine encephalitis, Eastern equine encephalitis, Western equine encephalitis, severe acute respiratory syndrome (SARS), parainfluenza, respiratory syncytial, Punta Toro, Tacaribe and pachindae.

In a some embodiments, the compounds of the invention are used to treat or prevent a viral infection associated with a virus. In some embodiments, the viral infection comprises infection with one or more type of virus. In some embodiments, the viral infection comprises infection by one or more viruses selected from the group consisting of orthmyxoviridae, Paramyxoviridae, arenaviridae, bunyaviridae, flaviviridae, filoviridae, togaviridae, picornaviridae, and coronaviridae viruses. In some embodiments, the viral infection comprises infection by one or more viruses selected from the group consisting of adenovirus, rhinovirus, hepatitis, immunodeficiency virus, polio, measles, Ebola, Coxsackie, Rhino, West Nile, small pox, encephalitis, yellow fever, Dengue fever, influenza (including human, avian, and swine), lassa, lymphocytic choriomeningitis, junin, machuppo, guanarito, hantavirus, Rift Valley Fever, La Crosse, California encephalitis, Crimean-Congo, Marburg, Japanese Encephalitis, Kyasanur Forest, Venezuelan equine encephalitis, Eastern equine encephalitis, Western equine encephalitis, severe acute respiratory syndrome (SARS), parainfluenza, respiratory syncytial, Punta Toro, Tacaribe and pachindae viruses.

In some embodiments, the viral infection comprises infection by one or more viruses selected from the group consisting of adenovirus, Dengue fever, influenza A and influenza B (including human, avian, and swine), junin, measles, parainfluenza, Pichinde, punta toro, respiratory syncytial, rhinovirus, Rift Valley Fever, severe acute respiratory syndrome (SARS), Tacaribe, Venezuelan equine encephalitis, West Nile and yellow fever viruses.

In some embodiments, the virus is Ebola, Marburg, yellow fever, influenza A or influenza B. In some embodiments, the virus is Ebola. In some embodiments, the virus is Marburg. In some embodiments, the virus is yellow fever. In some embodiments, the virus is influenza A or influenza B.

In some embodiments, the virus is West Nile or Dengue fever. In some embodiments the virus is West Nile. In some embodiments, the virus is Dengue fever.

In some embodiments, the compounds of the invention are used to inhibit the replication or infectivity of a virus. In some embodiments, the compounds of the invention are used to inhibit the growth of a cell infected with a virus. Examples of said viruses include, but are not limited to, viruses of the orthmyxoviridae, paramyxoviridae, arenaviridae, bunyaviridae, flaviviridae, filoviridae, togaviridae, picornaviridae, and coronaviridae families. Specific examples of viruses include, but are not limited to, adenovirus, rhinovirus, hepatitis, immunodeficiency virus, polio, measles, Ebola, Coxsackie, Rhino, West Nile, small pox, encephalitis, yellow fever, Dengue fever, influenza (including human, avian, and swine), lassa, lymphocytic choriomeningitis, junin, machuppo, guanarito, hantavirus, Rift Valley Fever, La Crosse, California encephalitis, Crimean-Congo, Marburg, Japanese Encephalitis, Kyasanur Forest, Venezuelan equine encephalitis, Eastern equine encephalitis, Western equine encephalitis, severe acute respiratory syndrome (SARS), parainfluenza, respiratory syncytial, Punta Toro, Tacaribe and pachindae.

Thus, in some embodiments, the virus is selected from the group consisting of viruses of the orthmyxoviridae, paramyxoviridae, arenaviridae, bunyaviridae, flaviviridae, filoviridae, togaviridae, picornaviridae, and coronaviridae families. In some embodiments, the viral infection comprises a virus selected from the group consisting of hepatitis, immunodeficiency virus, polio, measles, Ebola, Coxsackie, Rhino, West Nile, small pox, encephalitis, yellow fever, Dengue fever, influenza (including human, avian, and swine), lassa, lymphocytic choriomeningitis, junin, machuppo, guanarito, hantavirus, Rift Valley Fever, La Crosse, California encephalitis, Crimean-Congo, Marburg, Japanese Encephalitis, Kyasanur Forest, Venezuelan equine encephalitis, Eastern equine encephalitis, Western equine encephalitis, severe acute respiratory syndrome (SARS), parainfluenza, respiratory syncytial, Punta Toro, Tacaribe and pachindae viruses.

In some embodiments, the viral infection comprises a virus selected from the group consisting of adenovirus, Dengue fever, influenza A and influenza B (including human, avian, and swine), junin, measles, parainfluenza, Pichinde, punta toro, respiratory syncytial, rhinovirus, Rift Valley Fever, severe acute respiratory syndrome (SARS), Tacaribe, Venezuelan equine encephalitis, West Nile and yellow fever viruses.

In some embodiments, the virus is Ebola, Marburg, yellow fever, influenza A or influenza B. In some embodiments, the virus is Ebola. In some embodiments, the virus is Marburg. In some embodiments, the virus is yellow fever. In some embodiments, the virus is influenza A or influenza B.

In some embodiments, the virus is West Nile or Dengue fever. In some embodiments the virus is West Nile. In some embodiments, the virus is Dengue fever.

In some embodiments, the present invention provides a method for inhibiting a viral RNA or DNA polymerase in a subject comprising administering to said subject a therapeutically effective amount of a compound of formula I, or a pharmaceutically acceptable salt or hydrate thereof.

According to the Baltimore classification system, RNA polymerase viruses may be classified into groups such as, for example, double-stranded viruses, positive-sense single-stranded viruses, and negative-sense single stranded viruses. Positive-sense single-stranded families include, for example, coronaviridae, picornaviridae, togaviridae, flaviviridae, and the like. Negative-sense single-stranded families include, for example, paramyxoviridae, arenaviridae, bunyaviridae, orthomyxoviridae, filoviridae, and the like. Each of the virus families may be further classified into genera, species, and serotype (or subtype). Other designations for taxonomic designations of viruses are set forth by the classification guidelines according to the International Committee on Taxonomy of Viruses.

In some embodiments, the RNA polymerase is double-stranded. In some embodiments, the RNA polymerase is single-stranded. In some embodiments, the RNA polymerase is positive-sense single-stranded. In some embodiments, the RNA polymerase is negative-sense single-stranded.

In some embodiments, the methods of the present invention provide for broad spectrum inhibition of viruses and/or RNA polymerases from one or more family, genus, subtype, strain and/or serotype of virus. In some embodiments, the methods provide for broad spectrum treatment, suppression, or prevention of infection from one or more family, genus, subtype, strain, or serotype of virus. In some embodiments, the broad spectrum encompasses more than two families, genera, subtypes, strains and/or serotypes of virus.

In some embodiments, the present invention provides a method for inhibiting viral polymerases from one or more virus family, genus, subtype, serotype, or strain. In some embodiments, the present invention provides a method for treating, suppressing, and/or preventing a viral infection wherein the viral infection is a result of infection with one or more virus family, genus, subtype, serotype, or strain.

In some embodiments, the viral polymerases or viruses are from one or more virus genus. In some embodiments, the viral polymerases or viruses are from one or more virus species. In some embodiments, the viral polymerases or viruses are selected from one or more subtypes or serotypes. In some embodiments, the viral polymerases or viruses are selected from one or more strains.

In some embodiments, the RNA viral polymerase is selected from the group consisting of polymerases of the orthmyxoviridae, paramyxoviridae, arenaviridae, bunyaviridae, flaviviridae, filoviridae, togaviridae, picornaviridae, and coronaviridae families. In some embodiments, the RNA viral polymerase is selected from the group consisting of polymerases of the orthmyxoviridae, paramyxoviridae, arenaviridae, bunyaviridae, flaviviridae, and coronaviridae families. In some embodiments, the RNA viral polymerase comprises a polymerase selected from the group consisting of hepatitis, immunodeficiency virus, polio, measles, Ebola, Coxsackie, Rhino, West Nile, small pox, encephalitis, yellow fever, Dengue fever, influenza (including human, avian, and swine), lassa, lymphocytic choriomeningitis, junin, machuppo, guanarito, hantavirus, Rift Valley Fever, La Crosse, California encephalitis, Crimean-Congo, Marburg, Japanese Encephalitis, Kyasanur Forest, Venezuelan equine encephalitis, Eastern equine encephalitis, Western equine encephalitis, severe acute respiratory syndrome (SARS), parainfluenza, respiratory syncytial, Punta Toro, Tacaribe and pachindae viral polymerase.

In some embodiments, the RNA viral polymerase is selected from the group consisting of adenovirus, Dengue fever, influenza A and influenza B (including human, avian, and swine), junin, measles, parainfluenza, Pichinde, punta toro, respiratory syncytial, rhinovirus, Rift Valley Fever, severe acute respiratory syndrome (SARS), Tacaribe, Venezuelan equine encephalitis, West Nile and yellow fever viral polymerase.

In some embodiments, the RNA viral polymerase is Ebola, Marburg, yellow fever, influenza A or influenza B viral polymerase. In some embodiments, the RNA viral polymerase is Ebola viral polymerase. In some embodiments, the RNA viral polymerase is Marburg viral polymerase. In some embodiments, the RNA viral polymerase is yellow fever viral polymerase. In some embodiments, the RNA viral polymerase is influenza A viral polymerase or influenza B viral polymerase. In some embodiments, the viral polymerase is West Nile or Dengue fever viral polymerase. In some embodiments the viral polymerase is West Nile viral polymerase. In some embodiments, the viral polymerase is Dengue fever viral polymerase.

In some embodiments, the viruses are selected from the group consisting of orthmyxoviridae, paramyxoviridae, arenaviridae, bunyaviridae, flaviviridae, filoviridae, togaviridae, picornaviridae, and coronaviridae families. In some embodiments, the viruses are selected from the group consisting of hepatitis, immunodeficiency virus, polio, measles, Ebola, Coxsackie, Rhino, West Nile, small pox, encephalitis, yellow fever, Dengue fever, influenza (including human, avian, and swine), lassa, lymphocytic choriomeningitis, junin, machuppo, guanarito, hantavirus, Rift Valley Fever, La Crosse, California encephalitis, Crimean-Congo, Marburg, Japanese Encephalitis, Kyasanur Forest, Venezuelan equine encephalitis, Eastern equine encephalitis, Western equine encephalitis, severe acute respiratory syndrome (SARS), parainfluenza, respiratory syncytial, Punta Toro, Tacaribe and pachindae.

In some embodiments, the viruses are selected from the group consisting of adenovirus, Dengue fever, influenza A and influenza B (including human, avian, and swine), junin, measles, parainfluenza, Pichinde, punta toro, respiratory syncytial, rhinovirus, Rift Valley Fever, severe acute respiratory syndrome (SARS), Tacaribe, Venezuelan equine encephalitis, West Nile and yellow fever viruses.

In some embodiments, the virus is Ebola, Marburg, yellow fever, influenza A or influenza B. In some embodiments, the virus is Ebola. In some embodiments, the virus is Marburg. In some embodiments, the virus is yellow fever. In some embodiments, the virus is influenza A or influenza B.

In some embodiments, the virus is West Nile or Dengue fever. In some embodiments the virus is West Nile. In some embodiments, the virus is Dengue fever.

The genome of the influenza A virus has an RNA-dependent RNA polymerase, which catalyzes viral RNA transcription and replication. Because the transcription and replication of the virus depends on the activity of RNA polymerase, this enzyme has become of interest as a target for development of new anti-viral compounds in the wake of the recent emergence of drug resistant viruses. Viruses may develop resistance to one drug upon treatment, thus decreasing the efficacy of the drug and requiring the subject to be treated with another antiviral drug. A drug or treatment that exhibits simultaneous efficacy against a broad spectrum of viral strains would thus be useful.

In addition, the composition or method may further comprise one or more additional anti-viral agents in combination with a compound of formula I. Examples of such anti-viral agents include, but are not limited to, Cytovene, Ganciclovir, trisodium phosphonoformate, ribavirin, interferon, d4T, ddI, AZT, and Amantadine, Rimandatine, and other anti-influenza agents; Acyclovir, and related agents, Foscarnet and other anti-herpes virus agents. Non-limiting examples of neuraminidase inhibitors include laninamivir, oseltamivir, zanamivir, and peramivir.

Compounds that relate to inhibition of influenza polymerase are described, for example, in U.S. Pat. Nos. 7,388, 002; 7,560,434; and in U.S. patent application Ser. No. 12/440,697 (published as U.S. Patent Publication No. 20100129317); and Ser. No. 12/398,866 (published as U.S. Patent Publication No. 20090227524), each of which herein incorporated by reference in its entirety. Currently, there is one influenza polymerase inhibitor in clinical trials, known as T-705 (favipiravir; 6-fluoro-3-hydroxy-2-pyrazinecarboxamide). T-705 possesses potent and broad spectrum antiviral activity against multiple strains of influenza virus infection in vitro and in vivo (Kiso et al., *PNAS* 2010, 107, 882-887; herein incorporated by reference in its entirety). T-705 is characterized by a mechanism of action that is different from most anti-influenza viral drugs.

Another class of compounds used as anti-virals are M2 inhibitors (See, Pielak, R., Schnell, J., & Chou, J. (2009) *Proceedings of the National Academy of Sciences,* 106 (18), 7379-7384 (herein incorporated by reference in its entirety). Exemplary members of this class include amantadine and rimantadine.

Thus, in some embodiments, the methods of the invention further comprise administration of one or more additional anti-viral agents.

In some embodiments, an additional anti-viral agent is selected from the group consisting of Cytovene, Ganciclovir, trisodium phosphonoformate, ribavirin, interferon, d4T, ddI, AZT, and amantadine, rimandatine, T-705 and other anti-influenza agents; Acyclovir, and related agents, Foscarnet and other anti-herpes virus agents.

In some embodiments, an additional anti-viral agent is an anti-influenza agent. In some embodiments, an additional anti-viral agent is a neuraminidase inhibitor. In some embodiments, an additional anti-viral agent is selected from the group consisting of laninamivir, oseltamivir, zanamivir, and peramivir. In some embodiments, an additional anti-viral agent is paramivir. In some embodiments, an additional anti-viral agent is laninamivir. In some embodiments, an additional anti-viral agent is oseltamivir. In some embodiments, an additional anti-viral agent is zanamivir.

In some embodiments, an additional anti-viral agent is an M2 inhibitor. In some embodiments, an additional anti-viral agent is selected from the group consisting of amantadine and rimandatine.

In some embodiments, the methods of the invention comprise administration of two additional anti-viral agents. In some embodiments, the additional anti-viral agents are a neuraminidase inhibitor and an M2 inhibitor. In some embodiments, the additional anti-viral agents are selected from the groups consisting of 1) laninamivir, oseltamivir, zanamivir, and peramivir; and 2) amantadine and rimandatine. In some embodiments, the additional antiviral agents are peramivir and amantadine. In some embodiments, the additional antiviral agents are peramivir and rimandatine.

The present invention provides methods for inhibiting a viral RNA or DNA polymerase comprising contacting the polymerase with an effective inhibitory amount of the compound of formula I, or a pharmaceutically acceptable salt or solvate thereof.

In some embodiments, the present invention provides a method for treating a subject suffering from a viral infection comprising administering to said subject a therapeutically effective amount of a compound of formula I, or pharmaceutically acceptable salt or hydrate thereof.

In some embodiments, the present invention provides a method for suppressing a viral infection in a subject comprising administering to the subject a therapeutically effective amount of a compound of formula I, or pharmaceutically acceptable salt or hydrate thereof.

In some embodiments, the present invention provides a method for treating a subject suffering from an RNA viral infection which comprises administering to said subject a therapeutically effective amount of a compound of formula I, or pharmaceutically acceptable salt or solvate thereof.

In some embodiments, the viral infection is comprises infection by one or more viruses.

In some embodiments, the viral infections are infections selected from viruses of the orthmyxoviridae, paramyxoviridae, arenaviridae, bunyaviridae, flaviviridae, filoviridae, togaviridae, picornaviridae, or coronaviridae families, or any combination thereof. In some embodiments, the viral infections are infections selected from viruses of hepatitis, immunodeficiency virus, polio, measles, Ebola, Coxsackie, Rhino, West Nile, small pox, encephalitis, yellow fever, Dengue fever, influenza (including human, avian, and swine), lassa, lymphocytic choriomeningitis, junin, machuppo, guanarito, hantavirus, Rift Valley Fever, La Crosse, California encephalitis, Crimean-Congo, Marburg, Japanese Encephalitis, Kyasanur Forest, Venezuelan equine encephalitis, Eastern equine encephalitis, Western equine encephalitis, severe acute respiratory syndrome (SARS), parainfluenza, respiratory syncytial, Punta Toro, Tacaribe and pachindae, or any combination thereof.

In some embodiments, the viral infection comprises infection by one or more viruses selected from the group consisting of adenovirus, Dengue fever, influenza A and influenza B (including human, avian, and swine), junin, measles, parainfluenza, Pichinde, punta toro, respiratory syncytial, rhinovirus, Rift Valley Fever, severe acute respiratory syndrome (SARS), Tacaribe, Venezuelan equine encephalitis, West Nile and yellow fever viruses.

In some embodiments, the virus is Ebola, Marburg, yellow fever, influenza A or influenza B. In some embodiments, the virus is Ebola. In some embodiments, the virus is Marburg. In some embodiments, the virus is yellow fever. In some embodiments, the virus is influenza A or influenza B.

In some embodiments, the virus is West Nile or Dengue fever. In some embodiments the virus is West Nile. In some embodiments, the virus is Dengue fever.

In some embodiments, the viral infections are infections selected from viruses of influenza A, influenza B, PIV, RSV, Junin, Pichinde, Rift Valley Fever, Dengue Fever, measles, Yellow Fever, and SARS-CoV, or any combination thereof. In some embodiments, the viral infections are infections selected from influenza A and B, subtypes thereof, strains thereof, or any combination thereof. In some embodiments, the viral infections are infections selected from Ebola, Marburg, or yellow fever. In some embodiments, the viral infection is Ebola. In some embodiments, the viral infection is Marburg. In some embodiments, the viral infection is yellow fever. In some embodiments, the viral infection is West Nile or Dengue fever. In some embodiments the viral infection is West Nile. In some embodiments, the viral infection is Dengue fever.

In some embodiments, the disclosure provides for the use of pharmaceutical compositions and/or medicaments comprised of the compound of formula I, or a pharmaceutically acceptable salt or hydrate thereof, in a method of treating a viral infection, and/or disease state, and/or condition caused by or related to such viral infection.

In some embodiments, the method of treatment comprises the steps of: i) identifying a subject in need of such treatment; (ii) providing a compound of formula I, or a pharmaceutically acceptable salt or hydrate thereof, or a composition comprising a compound of formula I, or a pharmaceutically acceptable salt or hydrate thereof; and (iii) administering said compound or composition in a therapeutically effective amount to treat the viral infection in the subject or to inhibit the activity of viral DNA or RNA polymerase in a subject in need of such treatment.

In some embodiments, the treatment efficacy results from the inhibition of a viral DNA or RNA polymerase. In some embodiments, the treatment efficacy results from inhibiting viral polymerases from one or more virus family.

In some embodiments, the viral polymerases or viruses are from one or more virus genus. In some embodiments, the viral polymerases or viruses are from one or more virus species. In some embodiments, the viral polymerases or viruses are selected from one or more subtype, serotype, or strain.

In some embodiments, the method is performed in vivo.

In some embodiments, the subject is a mammal. In some embodiments, the subject is a human. In some embodiments, the subject is avian. In some embodiments, the subject is a swine or pig.

In some embodiments, the bodily fluid is blood. In some embodiments, the bodily fluid is plasma. In some embodiments, the bodily fluid is blood serum.

In some embodiments, the compound or composition is administered intravenously, interperitonealy, intramuscularly or orally.

In some embodiments, the compound or composition is administered intravenously.

In some embodiments, the compound or composition is administered intraperitonealy.

In some embodiments, the compound or composition is administered intramuscularly.

In some embodiments, the compound or composition is administered orally.

The methods comprise administering to the subject a therapeutically effective amount of a compound of formula I, or a pharmaceutically acceptable salt thereof, or a composition comprising a compound of formula I, or a pharmaceutically acceptable salt thereof, and a pharmaceutically acceptable carrier. The pharmaceutically acceptable carriers are well-known to those skilled in the art, and include, for example, adjuvants, diluents, excipients, fillers, lubricants and vehicles. Often, the pharmaceutically acceptable carrier is chemically inert toward the active compounds and is non-toxic under the conditions of use. Examples of pharmaceutically acceptable carriers may include, for example, water or saline solution, polymers such as polyethylene glycol, carbohydrates and derivatives thereof, oils, fatty acids, or alcohols. In some embodiments, the carrier is saline or water. In some embodiments, the carrier is saline. In some embodiments, the carrier is water.

In some embodiments, the method of prevention or suppression of the viral infection or disease state comprises the steps of: i) identifying a subject in need of such treatment; (ii) providing a compound of formula I, or a pharmaceutically acceptable salt or hydrate thereof, or a composition comprising a compound of formula I, or a pharmaceutically acceptable salt or hydrate thereof; and (iii) administering said compound or composition in a therapeutically effective amount to prevent or suppress the viral infection or disease state in the subject or to inhibit the activity of viral DNA or RNA polymerase in a subject in need of such treatment.

The compounds of the present invention are prepared in different forms, such as salts, hydrates, solvates, tautomers or complexes, and the invention includes methods encompassing all variant forms of the compounds.

In some embodiments, the methods of the invention comprise pharmaceutically acceptable salts of the compound of formula I. A compound of formula I also may be formulated as a pharmaceutically acceptable salt, e.g., acid addition salt, and complexes thereof. The preparation of such salts can facilitate the pharmacological use by altering the physical characteristics of the agent without preventing its physiological effect. Examples of useful alterations in physical properties include, but are not limited to, lowering the melting point to facilitate transmucosal administration and increasing the solubility to facilitate administering higher concentrations of the drug.

The subjects of the invention are in vitro and in vivo systems, including, for example, isolated or cultured cells or tissues, non-cellular in vitro assay systems and animals (e.g., an amphibian, a bird, a fish, a mammal, a marsupial, a human, a domestic animal such as, for example, a cat, dog, monkey, mouse or rat; or a commercial animal such as, for example, a cow or pig).

The compounds of the invention may be formulated into pharmaceutical compositions for administration to subjects in a biologically compatible form suitable for administration in vivo. According to another aspect, the present invention provides a pharmaceutical composition comprising compounds of formula I in admixture with a pharmaceutically acceptable diluent and/or carrier. The pharmaceutically-acceptable carrier must be "acceptable" in the sense of being compatible with the other ingredients of the composition and not deleterious to the recipient thereof. The pharmaceutically-acceptable carriers employed herein may be selected from various organic or inorganic materials that are used as materials for pharmaceutical formulations and which are incorporated as analgesic agents, buffers, binders, disintegrants, diluents, emulsifiers, excipients, extenders, glidants, solubilizers, stabilizers, suspending agents, tonicity agents, vehicles and viscosity-increasing agents. Pharmaceutical additives, such as antioxidants, aromatics, colorants, flavor-improving agents, preservatives, and sweeteners, may also be added. Examples of acceptable pharmaceutical carriers include carboxymethyl cellulose, crystalline cellulose, glycerin, gum arabic, lactose, magnesium stearate, methyl cellulose, powders, saline, sodium alginate, sucrose, starch, talc and water, among others. In some embodiments, the term "pharmaceutically acceptable" means approved by a regulatory agency of the Federal or a state government or listed in the U.S. Pharmacopeia or other generally recognized pharmacopeia for use in animals, and more particularly in humans.

Surfactants such as, for example, detergents, are also suitable for use in the formulations. Specific examples of surfactants include polyvinylpyrrolidone, polyvinyl alcohols, copolymers of vinyl acetate and of vinylpyrrolidone, polyethylene glycols, benzyl alcohol, mannitol, glycerol, sorbitol or polyoxyethylenated esters of sorbitan; lecithin or sodium carboxymethylcellulose; or acrylic derivatives, such as methacrylates and others, anionic surfactants, such as alkaline stearates, in particular sodium, potassium or ammonium stearate; calcium stearate or triethanolamine stearate; alkyl sulfates, in particular sodium lauryl sufate and sodium cetyl sulfate; sodium dodecylbenzenesulphonate or sodium dioctyl sulphosuccinate; or fatty acids, in particular those derived from coconut oil, cationic surfactants, such as water-soluble quaternary ammonium salts of formula $N^+R'R''R'''R''''Y^-$, in which the R radicals are identical or different optionally hydroxylated hydrocarbon radicals and $Y^-$ is an anion of a strong acid, such as halide, sulfate and sulfonate anions; cetyltrimethylammonium bromide is one of the cationic surfactants which can be used, amine salts of formula $N^+R'R''R'''$, in which the R radicals are identical or different optionally hydroxylated hydrocarbon radicals; octadecylamine hydrochloride is one of the cationic surfactants which can be used, non-ionic surfactants, such as optionally polyoxyethylenated esters of sorbitan, in particular Polysorbate 80, or polyoxyethylenated alkyl ethers; polyethylene glycol stearate, polyoxyethylenated derivatives of castor oil, polyglycerol esters, polyoxyethylenated fatty alcohols, polyoxyethylenated fatty acids or copolymers of ethylene oxide and of propylene oxide, amphoteric surfactants, such as substituted lauryl compounds of betaine, When administered to a subject, the compounds of formula I and pharmaceutically acceptable carriers may be sterile. In some embodiments, water is a carrier when the compound of formula I is administered intravenously. In some embodiments, the carrier is a saline solution when the compound of formula I is administered intravenously. Aqueous dextrose and glycerol solutions may also be employed as liquid carriers, particularly for injectable solutions. Suitable pharmaceutical carriers may also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, polyethylene glycol 300, water, ethanol, polysorbate 20, and the like. The present compositions, if desired, may also contain minor amounts of wetting or emulsifying agents, or pH buffering agents.

The pharmaceutical formulations of the present invention are prepared by methods well-known in the pharmaceutical arts. For example, the compounds of formula I are brought into association with a carrier and/or diluent, as a suspension or solution. Optionally, one or more accessory ingredients (e.g., buffers, flavoring agents, surface active agents, and the like) also are added. The choice of carrier is determined by the solubility and chemical nature of the compounds, chosen route of administration and standard pharmaceutical practice. In some embodiments, the formulation comprises a compound of formula I and water. In some embodiments, the formulation comprises a compound of formula I and saline.

Additionally, the compounds of the present invention are administered to a human or animal subject by known procedures including, without limitation, oral administration, sublingual or buccal administration, parenteral administration, transdermal administration, via inhalation or intranasally, vaginally, rectally, and intramuscularly. The compounds of the invention are administered parenterally, by epifascial, intracapsular, intracranial, intracutaneous, intrathecal, intramuscular, intraorbital, intraperitoneal, intraspinal, intrasternal, intravascular, intravenous, parenchymatous, subcutaneous or sublingual injection, or by way of catheter. In some embodiments, the compound is administered to the subject by way of intramuscular delivery. In some embodiments, the compound is administered to the subject by way of intraperitoneal delivery. In some embodiments, the compound is administered to the subject by way of intravenous delivery. In some embodiments, the compound is administered orally.

For oral administration, a formulation of the compounds of the invention may be presented as capsules, tablets, powders, granules, or as a suspension or solution. Capsule formulations may be gelatin, soft-gel or solid. Tablets and capsule formulations may further contain one or more adjuvants, binders, diluents, disintegrants, excipients, fillers, or lubricants, each of which are known in the art. Examples of such include carbohydrates such as lactose or sucrose, dibasic calcium phosphate anhydrous, corn starch, mannitol, xylitol, cellulose or derivatives thereof, microcrystalline cellulose, gelatin, stearates, silicon dioxide, talc, sodium starch glycolate, acacia, flavoring agents, preservatives, buffering agents, disintegrants, and colorants. Orally administered compositions may contain one or more optional agents such as, for example, sweetening agents such as fructose, aspartame or saccharin; flavoring agents such as peppermint, oil of wintergreen, or cherry; coloring agents; and preservative agents, to provide a pharmaceutically palatable preparation.

For parenteral administration (i.e., administration by injection through a route other than the alimentary canal), the compounds of the invention may be combined with a sterile aqueous solution that is isotonic with the blood of the subject. Such a formulation is prepared by dissolving a solid active ingredient in water containing physiologically-compatible substances, such as sodium chloride, glycine and the like, and having a buffered pH compatible with physiological conditions, so as to produce an aqueous solution, then rendering said solution sterile. The formulation may be presented in unit or multi-dose containers, such as sealed ampules or vials. The formulation may be delivered by any mode of injection, including, without limitation, epifascial, intracapsular, intracranial, intracutaneous, intrathecal, intramuscular, intraorbital, intraperitoneal, intraspinal, intrasternal, intravascular, intravenous, parenchymatous, subcutaneous, or sublingual or by way of catheter into the subject's body.

Parenteral administration includes aqueous and non-aqueous based solutions. Examples of which include, for example, water, saline, aqueous sugar or sugar alcohol solutions, alcoholic (such as ethyl alcohol, isopropanol, glycols), ethers, oils, glycerides, fatty acids, and fatty acid esters. In some embodiments, water is used for parenteral administration. In some embodiments, saline is used for parenteral administration. Oils for parenteral injection include animal, vegetable, synthetic or petroleum based oils. Examples of sugars for solution include sucrose, lactose, dextrose, mannose, and the like. Examples of oils include mineral oil, petrolatum, soybean, corn, cottonseed, peanut, and the like. Examples of fatty acids and esters include oleic acid, myristic acid, stearic acid, isostearic acid, and esters thereof.

For transdermal administration, the compounds of the invention are combined with skin penetration enhancers, such as propylene glycol, polyethylene glycol, isopropanol, ethanol, oleic acid, N-methylpyrrolidone and the like, which increase the permeability of the skin to the compounds of the invention and permit the compounds to penetrate through the skin and into the bloodstream. The compound/enhancer compositions also may be further combined with a polymeric substance, such as ethylcellulose, hydroxypropyl cellulose, ethylene/vinylacetate, polyvinyl pyrrolidone, and the like, to provide the composition in gel form, which are dissolved in a solvent, such as methylene chloride, evaporated to the desired viscosity and then applied to backing material to provide a patch.

In some embodiments, the composition is in unit dose form such as a tablet, capsule or single-dose vial. Suitable unit doses, i.e., therapeutically effective amounts, may be determined during clinical trials designed appropriately for each of the conditions for which administration of a chosen compound is indicated and will, of course, vary depending on the desired clinical endpoint.

The present invention also provides articles of manufacture for treating and preventing disorders, such as viral disorders, in a subject. The articles of manufacture comprise a pharmaceutical composition of the compounds of formula I, optionally further containing at least one additional antiviral compound, as described herein. The articles of manufacture are packaged with indications for various disorders that the pharmaceutical compositions are capable of treating and/or preventing. For example, the articles of manufacture comprise a unit dose of a compound disclosed herein that is capable of treating or preventing a certain disorder, and an indication that the unit dose is capable of treating or preventing a certain disorder, for example a viral infection.

In accordance with a method of the present invention, the compounds of formula I are administered to the subject (or are contacted with cells of the subject) in an amount effective to limit or prevent a decrease in the level of virus in the subject, particularly in cells of the subject. This amount is readily determined by the skilled artisan, based upon known procedures, including analysis of titration curves established in vivo and methods and assays disclosed herein. In some embodiments, a suitable amount of the compounds of the invention effective to limit or prevent an increase in the level of viral particles in the subject ranges from about 0.01 mg/kg/day to about 1000 mg/kg/day, and/or is an amount sufficient to achieve plasma levels ranging from about 300 ng/mL to about 1000 ng/mL or greater. In some embodiments, the amount of compounds from the invention ranges from about 5 mg/kg/day to about 1000 mg/kg/day. In some embodiments, from about 0.01 mg/kg/day to about 500 mg/kg/day is administered. In some embodiments, from about 0.01 mg/kg/day to about 300 mg/kg/day is administered. In some embodiments, from about 0.01 mg/kg/day to about 200 mg/kg/day is administered. In some embodiments, from about 0.05 mg/kg/day to about 100 mg/kg/day is administered. In some embodiments, from about 0.05 mg/kg/day to about 50 mg/kg/day is administered. In some embodiments, from about 0.05 mg/kg/day to about 30 mg/kg/day is administered. In some embodiments, from about 0.05 mg/kg/day to about 10 mg/kg/day is administered.

The precise dose to be employed in the compositions will also depend on the route of administration, and the seriousness of the infection or disorder, and should be decided according to the judgment of the practitioner and each patient's circumstances. However, suitable effective dosage ranges for intramuscular administration are generally about 0.5 to about 1000 mg of the compound of formula I per kilogram body weight. In specific embodiments, the i.m. dose is about 500 to about 1000 mg/kg, about 300 to about 500 mg/kg, about 200 to about 300 mg/kg, about 100 to about 200 mg/kg, about 50 to about 100 mg/kg, about 10 to about 50 mg/kg, or about 5 to about 10 mg/kg (or the equivalent doses expressed per square meter of body surface area). Alternatively, a suitable dose range for i.v. administration may be obtained using doses of about 5 to about 1000 mg, without adjustment for a patient's body weight or body surface area. Alternatively, a suitable dose range for i.p. administration may be obtained using doses of about 5 to about 1000 mg, without adjustment for a patient's body weight or body surface area. Oral compositions may contain about 10% to about 95% by weight of one or more compound of formula I alone or in combination with another therapeutic agent. In some embodiments of the invention, suitable dose ranges for oral, i.p., or i.m. administration are generally about 5 to about 1000 mg, preferably about 5 to about 500 mg of compound per kilogram body weight or their equivalent doses expressed per square meter of body surface area. In some embodiments the oral, i.p., or i.m. dose is about 5 to about 50 mg/kg, about 50 to about 80 mg/kg, about 80 to about 150 mg/kg, about 150 to about 250 mg/kg, about 250 to about 350 mg/kg, about 350 to about 450 mg/kg, about 450 to about 550 mg/kg, about 550 to about 700 mg/kg, about 700 to about 1000 mg/kg (or the equivalent doses expressed per square meter of body surface area). In some embodiments, a suitable dose range for oral, i.p., or i.m. administration is from about 5 to about 2000 mg, without adjustment for a patient's body weight or body surface area. Other effective doses may be extrapolated from dose-response curves derived from in vitro or animal model test systems. Such animal models and systems are well known in the art.

In certain aspects, an "effective amount" of a compound in the context of a viral infection is an amount sufficient to reduce one or more of the following steps of a the life cycle of a virus: the docking of the virus particle to a cell, the introduction of viral genetic information into a cell, the expression of viral proteins, the production of new virus particles and the release of virus particles from a cell by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or 100%. In some embodiments, an effective amount of a compound in the context of a viral infection reduces the replication, multiplication or spread of a virus by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or 100%. In some embodiments, an effective amount of a compound in the context of a viral infection increases the survival rate of infected subjects by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or 100%.

Those skilled in the art will recognize, or be able to ascertain using no more than routine experimentation, many equivalents to the specific embodiments of the invention described herein. Such equivalents are intended to be within the scope of the present invention.

The invention is further described by the following non-limiting Examples.

EXAMPLES

Example 1

Synthesis of (2S,3S,4R,5R)-2-(4-Amino-5H-pyrrolo[3,2-d]pyrimidin-7-yl)-5-(hydroxymethyl) pyrrolidine-3,4-diol [compound 1 (formula I, wherein A=NH$_2$ and B=H) as the HCl salt]

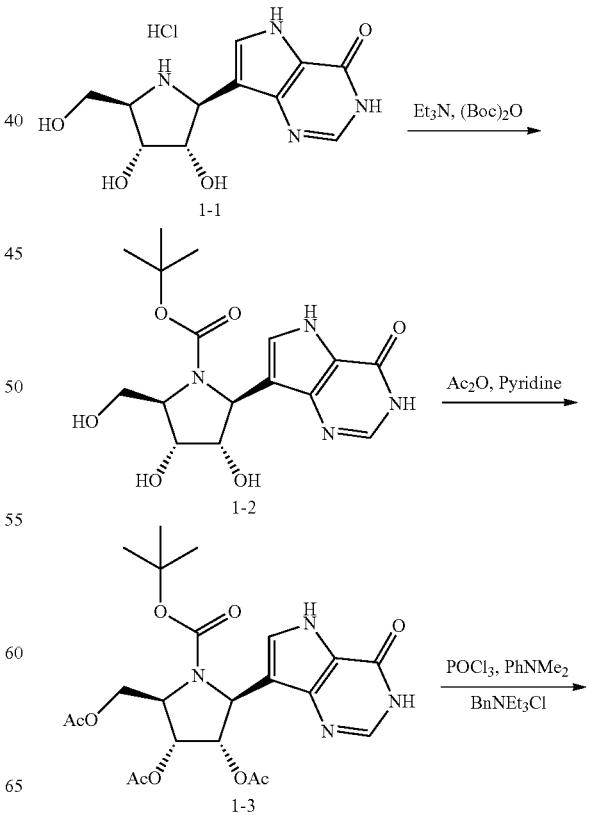

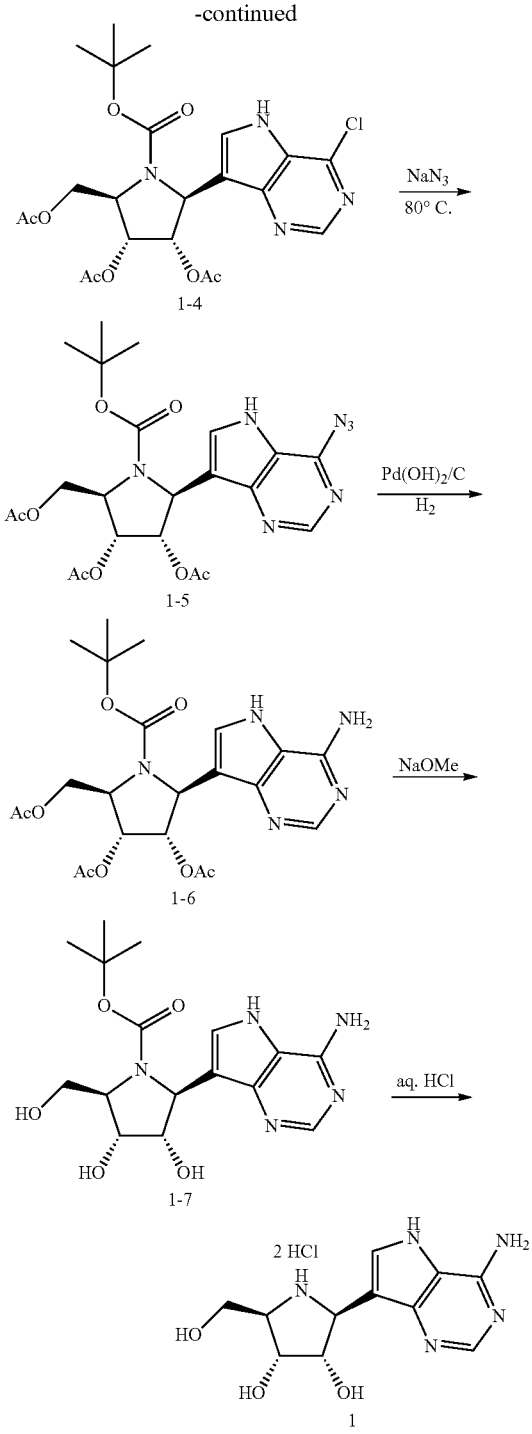

reaction mixture was stirred at room temperature overnight. The solid product was collected by filtration, washed with water, and dried in vacuum to afford (2R,3R,4S,5S)-tert-butyl 3,4-dihydroxy-2-(hydroxymethyl)-5-(4-oxo-4,5-dihydro-3H-pyrrolo[3,2-d]pyrimidin-7-yl)pyrrolidine-1-carboxylate (1-2) (100%) as a white solid. $^1$H NMR (300 MHz, DMSO) δ7.85 (s, 1H), 7.35 (s, 1H), 4.73-4.53 (m, 1H), 4.29 (s, 1H), 4.03 (s, 1H), 3.97 (s, 1H), 3.70-3.53 (m, 2H), 1.36 and 1.04 (s, 3H, 6H for rotomers).

Step-2:

To a solution of (2R,3R,4S,5S)-tert-butyl 3,4-dihydroxy-2-(hydroxymethyl)-5-(4-oxo-4,5-dihydro-3H-pyrrolo[3,2-d]pyrimidin-7-yl)pyrrolidine-1-carboxylate (1-2) in pyridine (184 mmol, 2.26 mol) was added DMAP (0.79 g, 6.46 mmol) and acetic anhydride (107 mL, 1131 mmol) at room temperature. The reaction mixture was stirred at room temperature overnight. The reaction mixture was diluted with chloroform and washed with water, aqueous HCl, water, and aqueous saturated sodium bicarbonate. The organic layer was dried, filtered and concentrated in vacuum, to furnish (2R,3R,4S,5S)-2-(acetoxymethyl)-1-(tert-butoxycarbonyl)-5-(4-oxo-4,5-dihydro-3H-pyrrolo[3,2-d]pyrimidin-7-1)pyrrolidine-3,4-diyl diacetate (1-3) (150 g), which was pure enough to be used as such for next step. MS (ES$^+$) 493.1 (M+1), 515.1 (M+Na); (ES$^-$) 491.4 (M−1).

Step-3:

To a solution of (2R,3R,4S,5S)-2-(acetoxymethyl)-1-(tert-butoxycarbonyl)-5-(4-oxo-4,5-dihydro-3H-pyrrolo[3,2-d]pyrimidin-7- yl)pyrrolidine-3,4-diyl diacetate (1-3) (150 g, 300 mmol) in acetonitrile (660 mL) was added benzyltriethylammonium chloride (137 g, 600 mmol), dimethylaniline (57 mL, 450 mmol), followed by POCl$_3$ (164 mL, 1800 mmol) at room temperature. The reaction mixture was heated at 80° C. for 1 h. The reaction mixture was cooled to room temperature and concentrated to dryness under vacuum. The residue obtained was dissolved in chloroform and washed with aqueous saturated sodium bicarbonate, brine, dried, filtered and concentrated to dryness. The residue of (2R,3R,4S,5S)-2-(acetoxymethyl)-1-(tert-butoxycarbonyl)-5-(4-chloro-5H-pyrrolo[3,2-d]pyrimidin-7-yl)pyrrolidine-3,4-diyl diacetate (1-4) was used as such in next step without purification. $^1$H NMR (300 MHz, DMSO) δ 12.54 (s, 1H), 8.65 (s, 1H), 7.92 (s, 1H), 5.85 (m, 1H), 5.45 (m, 1H), 5.10 (m, 1H), 4.49 (m, 2H), 4.07 (m, 1H), 2.07-1.99 (m, 9H), 1.19 (2 bs, 9H, rotomers).

Step-4:

To a solution of (2R,3R,4S,5S)-2-(acetoxymethyl)-1-(tert-butoxycarbonyl)-5-(4-chloro-5H-pyrrolo[3,2-d]pyrimidin-7-yl)pyrrolidine-3,4-diyl diacetate (1-4) (300 mmol) in DMF (540 mL) was added sodium azide (97.5 g, 1500 mmol) and heated at 80° C. overnight. The reaction mixture was concentrated in vacuum and the residue obtained was dissolved in chloroform. The chloroform layer was washed with water, dried, filtered and concentrated in vacuum. Purification by crystallization from (acetone:hexane=1:2) furnished (2R,3R,4S,5S)-2-(acetoxymethyl)-5-(4-azido-5H-pyrrolo[3,2-d]pyrimidin-7-yl)-1-(tert-butoxycarbonyl)pyrrolidine-3,4-diyl diacetate (1-5). $^1$H NMR (300 MHz, DMSO) δ 13.56-13.00 (bs, 1H), 9.86 (s, 1H), 7.95 (s, 1H), 5.78 (m, 1H), 5.40 (m, 1H), 5.26-5.14 (m, 1H), 4.54 (m, 1H), 4.42 (m, 1H), 4.16-4.03 (m, 1H), 2.06 (s, 3H), 2.02 (s, 6H), 1.14 (bs, 9H); MS (ES$^+$) 540.0 (M+1); (ES$^-$) 515.9 (M−1).

Step-5:

To a solution of (2R,3R,4S,5S)-2-(acetoxymethyl)-5-(4-azido-5H-pyrrolo[3,2-d]pyrimidin-7-yl)-1-(tert-butoxycarbonyl)pyrrolidine-3,4-diyl diacetate (1-5) (300 mmol) in methanol (1 L) was added Pd(OH)$_2$ (30 g). The reaction Step-1:

To a solution of 7-((2S,3S,4R,5R)-3,4-dihydroxy-5-(hydroxymethyl)pyrrolidin-2-yl)-3H-pyrrolo[3,2-d]pyrimidin-4(5H)-one (1-1) [(prepared according to procedure reported by Evans, Gary B.; Furneaux, Richard H.; Hutchison, Tracy L.; Kezar, Hollis S.; Morris, Philip E., Jr.; Schramm, Vern L.; Tyler, Peter C in Journal of Organic Chemistry (2001), 66(17), 5723-5730; herein incorporated by reference in its entirety) 115 g, 390 mmol] in water and methanol (1:1, 2.4 L) was added triethylamine (113 mL, 1.12 mol) at room temperature followed by (Boc)$_2$O (227 g, 1.04 mol). The mixture was hydrogenated at (160 psi) overnight, and filtered to remove catalyst through celite. The filtrate was concentrated in vacuum to furnish (2R,3R,4S,5S)-2-(acetoxymethyl)-5-(4-amino-5H-pyrrolo[3,2-d]pyrimidin-7-yl)-1-(tert-butoxycarbonyl)pyrrolidine-3,4- diyl diacetate (1-6) (113 g). $^1$H NMR (300 MHz, DMSO) δ 12.47-11.92 (m, 1H), 8.84-8.03 (m, 3H), 7.90-7.68 (m, 1H), 5.70-5.51 (m, 1H), 5.38 (m, 1H), 5.12 (m, 1H), 4.42 (m, 2H), 4.17-4.00 (m, 1H), 2.07 (s, 3H), 2.05 (s, 3H), 2.00 (s, 3H), 1.14 (s, 9H); MS (ES$^+$) 492.1 (M+1), (ES$^-$) 490.0 (M−1).

Step-6:

To a solution of (2R,3R,4S,5S)-2-(acetoxymethyl)-5-(4-amino-5H-pyrrolo[3,2-d]pyrimidin-7-yl)-1-(tert-butoxycarbonyl)pyrrolidine-3,4-diyl diacetate (1-6) (111 g, 226 mmol) in methanol (500 mL) was added NaOMe (25% w/w in methanol, 4.88 g, 22.6 mmol) at room temperature. The reaction mixture was stirred at room temperature for 3 h and concentrated in vacuum to give (2S,3S,4R,5R)-tert-butyl 2-(4-amino-5H-pyrrolo[3,2-d]pyrimidin-7-yl)-3,4-dihydroxy-5-(hydroxymethyl)pyrrolidine-1- carboxylate (1-7). $^1$H NMR (300 MHz, DMSO) δ 11.40-10.73 (bs, 1H), 8.01 (s, 1H), 7.39 (2s, 1H), 6.90 (s, 2H), 4.83 (m, 2H), 4.45 (m, 2H), 3.96 (s, 2H), 3.58 (m, 3H), 1.31 and 0.99 (s, 3H, 6H, rotomers); MS (ES$^+$) 366.0 (M+1), 388.0 (M+Na); (ES$^-$) 363.8 (M−1).

Step-7:

A solution of (2S,3S,4R,5R)-tert-butyl 2-(4-amino-5H-pyrrolo[3,2-d]pyrimidin-7-yl)-3,4-dihydroxy-5-(hydroxymethyl)pyrrolidine-1-carboxylate (1-7) aqueous HCl (160 mL of conc. HCl and 400 mL of water) was stirred at room temperature for 30 min and then concentrated in vacuum to dryness. The residue obtained was dissolved in water, treated with activated charcoal and refluxed for 30 min. The hot solution was filtered through celite and concentrated in vacuum to obtain a semi-solid product, which was recrystallized from water and ethanol to furnish (2S,3S,4R,5R)-2-(4-amino-5H-pyrrolo[3,2-d]pyrimidin-7-yl)-5-(hydroxymethyl)pyrrolidine-3,4-diol (1) (50 g, overall yield for 7 steps: 42.6%) as white crystal. $^1$H NMR (300 MHz, D$_2$O) δ 8.41 (s, 1H), 8.02 (s, 1H), 4.99 (d, J=9 Hz, 1H), 4.78 (m, 1H), 4.45 (dd, J=3, 1.5 Hz, 1H), 3.97 (m, 2H), 3.90 (m, 1H); MS (ES$^+$) 266.2 (M+1), (ES$^-$) 264.0 (M−1); Analysis: Calculated for $C_{11}H_{15}N_5O_3$.2 HCl: C, 39.07; H, 5.07; N, 20.71; Cl, 20.97. Found: C, 39.09; H, 5.10; N, 20.49; Cl, 20.84.

Example 2

Large-scale synthesis of (2S,3S,4R,5R)-2-(4-Amino-5H-pyrrolo[3,2-d]pyrimidin-7-yl)-5-(hydroxymethyl) pyrrolidine-3,4-diol [compound 1 (formula I, wherein A=NH$_2$ and B=H) as the HCl salt]

Step-1:

To a suspension of 7-((2S,3S,4R,5R)-3,4-dihydroxy-5-(hydroxymethyl)pyrrolidin-2-yl)-3H-pyrrolo[3,2-d]pyrimidin-4(5H)-one (1-1) [(prepared according to procedure reported by Evans, Gary B.; Furneaux, Richard H.; Hutchison, Tracy L.; Kezar, Hollis S.; Morris, Philip E., Jr.; Schramm, Vern L.; Tyler, Peter C in *Journal of Organic Chemistry* (2001), 66(17), 5723-5730), 500.0 g, 1.474 mol, 1 eq)] in a water:methanol mixture (1:1, 10.4 L) was added triethylamine (621 mL, 4.422 mol, 3.0 eq) at room temperature followed by (Boc)$_2$O (987 g, 4.53 mol, 3.1 eq). The reaction mixture became a clear colored solution after the addition of (Boc)$_2$O with slight increase of the internal temperature from 28° C. to 33° C. The solution started showing some turbidity after 1 hour of stirring. The solution was stirred at room temperature overnight. The solid product was collected by filtration and washed with water (5.0 L), dried at high vacuum at 50° C. to furnish (2R,3R,4S,5S)-tert-butyl 3,4-dihydroxy-2-(hydroxymethyl)-5-(4-oxo-4,5-dihydro-3H-pyrrolo[3,2-d]pyrimidin-7-yl)pyrrolidine-1-carboxylate (1-2) (482 g, 89%).

$^1$H NMR (300 MHz, DMSO) δ 11.92 (s, 2H), 7.81 (s, 1H), 7.32 (d, J=22.7 Hz, 1H), 5.73-5.20 (m, 1H), 5.05-4.91 (m, 1H), 4.87-4.76 (m, 1H), 4.74-4.49 (m, 1H), 4.33-4.17 (m, 1H), 4.09-3.86 (m, 2H), 3.64-3.48 (m, 2H), 1.39-1.00 (m, 9H); MS (ES+) 755.1 (2M+Na), (ES−) 731.7 (2M−1); Analysis; Calculated for $C_{16}H_{22}N_4O_6$: C, 52.45; H, 6.05; N, 15.29. Found: C, 52.24; H, 6.02; N, 15.05.

Step-2:

To a suspension of (2R,3R,4S,5S)-tert-butyl 3,4-dihydroxy-2-(hydroxymethyl)-5-(4-oxo-4,5-dihydro-3H-pyrrolo[3,2-d]pyrimidin-7-yl)pyrrolidine-1-carboxylate (1-2) (482 g, 1.32 mole, 1.0 equiv.) in pyridine (740 mL, 9.21 mole, 7 equiv.) was added DMAP (3.22 g, 26.32 mmol, 0.02 equiv.) and acetic anhydride (435 mL, 4.61 mmol, 3.5 eq) at room temperature. The internal temperature started rising upon the addition of the acetic anhydride therefore ice-water bath cooling was performed. Upon the total addition of the anhydride the temperature rose to 67° C. then decreased to room temperature. The ice water bath was removed after the reaction reached 25° C. The suspension did not give a clear solution but a lighter suspension was observed. The reaction mixture was stirred at room temperature for 14 h to yield a non-clear solution. A worked-up aliquot showed that there was no more starting material and two major spots by TLC (9:1 chloroform:methanol), MS shows two major peaks at (493.0, M+1) for product and tetraacetylated product (M+1=535). The reaction mixture was diluted with 3.0 L of chloroform, stirred for 10 minutes then added 2.0 L of deionized water. A waxy white product was formed in the aqueous organic phase interface. This product remained in the aqueous phase after the partition was done. The organic phase was separated and washed again with 2.0 L of water. The combined water washes were back extracted with 1.0 of chloroform. The combined organic phases were washed with aqueous 2.0 N HCl (2×1.0 L), water (2×1.0 L), saturated sodium bicarbonate (2×1.0 L) and brine (2×1.0 L). The organic layer was dried over MgSO$_4$, filtered and concentrated to dryness under vacuum and 50-55° C. water bath. The vacuum was switched to a high vacuum oil pump until no more distillate was seen to furnish a dense syrupy product. The product was left at high vacuum oil pump for 14 hrs to minimize the residual pyridine. A combination of solid foam which turned into a nice white solid and a dense residue of (2R,3R,4S,5S)-2-(acetoxymethyl)-1-(tert-butoxycarbonyl)-5-(4-oxo-4,5-dihydro-3H-pyrrolo[3,2-d]pyrimidin-7-yl)pyrrolidine-3,4-diyl diacetate (1-3) was obtained (715, 110% yield). This percentage reflects the amount of tetraacetylated compound. The product was pure enough to be used as is for next step. An analytical sample was prepared by purification of the mixture using flash column chromatography [silica gel, eluting with 0-100% (9:1) ethyl acetate/methanol in hexane] to furnish (2R,3R,4S,5S)-2-(acetoxymethyl)-1-(tert-butoxycarbonyl)-5-(4-oxo-4,5-dihydro-3H-pyrrolo[3,2-d]pyrimidin-7-yl)pyrrolidine-3,4-diyl diacetate (1-3) as a white solid; $^1$HNMR (300 MHz, DMSO) δ 12.13 (s, 1H, D2O Exchangeable), 11.98 (s, 1H, D$_2$O exchangeable), 7.82 (s, 1H), 7.29 (s, 1H), 5.76 (s, 1H), 5.37 (t, J=4.5 Hz, 1H), 4.99 (s, 1H), 4.55 (dd, J=11.3, 6.6 Hz, 1H), 4.34 (d, J=8.3 Hz, 1H), 4.03 (q, J=7.1 Hz, 1H), 2.01 (d, J=12.6 Hz, 9H), 1.23 (dd, J=39.9, 32.8 Hz, 9H); MS (ES+) 493.0 (M+1); (ES−) 526.7 (M+Cl); Analysis: Calculated for $C_{22}H_{28}N_4O_9$: C, 53.65; H, 5.73; N, 11.38. Found: C, 53.18; H, 5.89; N, 11.10.

Step-3:

To a solution of (2R,3R,4S,5S)-2-(acetoxymethyl)-1-(tert-butoxycarbonyl)-5-(4-oxo-4,5-dihydro-3H-pyrrolo[3,2-d]pyrimidin-7-yl)pyrrolidine-3,4-diyl diacetate (1-3) (622 g, 1.26 mol, 1.0 eq) in acetonitrile (2.75 L) was added benzyltriethylammonium chloride (575 g, 2.5 mol, 2.0 eq), dimethylaniline (240 mL, 1.9 mol, 1.5 eq), followed by $POCl_3$ (706 mL, 7.58 mol, 6.0 eq) at room temperature. A clear light yellow colored solution was obtained. The reaction mixture was slowly heated up to 80° C. and held at this temperature for 10 minutes. TLC in 9:1 chloroform:methanol shows that the reaction is >98% completed. The black homogeneous solution was cooled down to 50.0° C. and concentrated under vacuum (water bath 70-73° C.) to remove $POCl_3$ the residue was put under oil pump high vacuum until no more distillate was seen. The residue was dissolved in 3.0 L of chloroform and quickly washed carefully with aqueous saturated sodium bicarbonate until a neutral pH was obtained. The organic layer was separated washed with water (2 L), brine (2 L), dried over $MgSO_4$, filtered and concentrated in vacuum to dryness (water bath at 50-53° C.). The black product of (2R,3R,4S,5S)-2-(acetoxymethyl)-1-(tert-butoxycarbonyl)-5-(4-chloro-5H-pyrrolo[3,2-d]pyrimidin-7-yl)pyrrolidine-3,4-diyl diacetate (1-4) was used as is in next step without purification.

Step-4:

To a solution of (2R,3R,4S,5S)-2-(acetoxymethyl)-1-(tert-butoxycarbonyl)-5-(4-chloro-5H-pyrrolo[3,2-d]pyrimidin-7-yl)pyrrolidine-3,4-diyl diacetate (1-4) (622 g, 1.26 mol, 1 eq) in DMF (1.5 L) was added sodium azide (411 g, 6.32 mol, 5 equiv.) and heated with stirring at 60° C. for 10 hours at which time the reaction has gone to completion (TLC in 9:1 chloroform methanol and 1:1 hexane:ethyl acetate). The reaction was cooled to 25° C., dumped in ice (2 L) and extracted with chloroform (2×1 L). The chloroform layers were combined washed with water (2×2 L), brine (2 L), dried, filtered and concentrated in vacuum (water bath 70-80° C.) to yield a black sludge. Purification of the sludge was achieved by column chromatography (987 g of black sludge, 8×30 inch column, ½ full silica gel, elution profile hexane:ethyl acetate; 9:1 (40.0 L); 7:3 (20.0 L); 6:4 (20.0 L); 1:1 (20 L); 4:6 (20.0 L) and 2:8 (20.0 L); The appropriate fractions were pooled and concentrated in vacuum (water bath 50.0° C.) to furnish (2R,3R,4S,5S)-2-(acetoxymethyl)-5-(4-azido-5H-pyrrolo[3,2-d]pyrimidin-7-yl)-1-(tert-butoxycarbonyl)pyrrolidine-3,4-diyl diacetate (1-5) (407.05 g, 62.3% yield for two steps) as a dense reddish colored honey-like product. An analytical sample was prepared by purification of the mixture by flash column chromatography [0-100% ethyl acetate in hexane] to furnish (2R,3R,4S,5S)-2-(acetoxymethyl)-5-(4-azido-5H-pyrrolo[3,2-d]pyrimidin-7-yl)-1-(tert-butoxycarbonyl)pyrrolidine-3, 4-diyl diacetate (1-5) as an orange solid. $^1$HNMR (300 MHz, DMSO) δ 13.08 (d, J=155.6 Hz, 1H, $D_2O$ exchangeable), 9.86 (s, 1H), 7.61 (d, J=76.8 Hz, 1H), 5.78 (t, J=4.5 Hz, 1H), 5.41 (t, J=4.3 Hz, 1H), 5.21 (s, 1H), 4.55 (dd, J=11.4, 6.4 Hz, 1H), 4.41 (dd, J=11.4, 3.9 Hz, 1H), 4.07 (d, J=16.5 Hz, 1H), 2.06 (s, 3H), 2.01 (d, J=9.9 Hz, 6H), 1.23 (dd, J=39.8, 32.7 Hz, 9H); MS (ES+) 518.0 (M+H), 540 (M+23); (ES−) 516.4 (M−1); Analysis: Calculated for $C_{22}H_{27}N_7O_8$: C, 51.06; H, 5.26; N, 18.95 Found: C, 50.97; H, 5.30; N, 18.62.

Step-5:

(2R,3R,4S,5S)-2-(acetoxymethyl)-5-(4-azido-5H-pyrrolo[3,2-d]pyrimidin-7-yl)-1-(tert-butoxycarbonyl)pyrrolidine-3,4-diyl diacetate (1-5) was reduced in three different batches as follows Batch 1: To a 2.0 L Parr hydrogenator, Teflon insert was added (2R,3R,4S,5S)-2-(acetoxymethyl)-5-(4-azido-5H-pyrrolo[3,2-d]pyrimidin-7-yl)-1-(tert-butoxycarbonyl)pyrrolidine-3,4-diyl diacetate (1-5) (108.01 g, 300 mmol in methanol, 800 mL), $Pd(OH)_2$ (21.6 g, 20% w/w).

Batch 2: To a 2.0 L Parr hydrogenator, Teflon insert was added (1-5) (140.70 g, 271.9 mmol in methanol, 1.0 L), $Pd(OH)_2$ (28.14 g, 20% w/w).

Batch 3: To a 2.0 L Parr hydrogenator, Teflon insert was added (1-5) (140.7 g, 271.9 mmol in methanol, 1.0 L), $Pd(OH)_2$ (28.14 g, 20% w/w).

The reaction mixtures were hydrogenated at 150 psi for 15-18 hours. The reaction mixture was filtered to remove the catalyst through celite. The filtrate was concentrated in vacuum (water bath 60-70° C.) until constant weight to furnish a dark colored product (2R, 3R, 4S, 5S)-2-(acetoxymethyl)-5-(4-amino-5H-pyrrolo[3, 2-d]pyrimidin-7-yl)-1-(tert-butoxycarbonyl) pyrrolidine-3, 4-diyl diacetate (1-6) (328.8 g, 89%). The product was pure enough to be used as is for next step. An analytical sample was prepared by purification of the mixture using flash column chromatography (0-10% methanol in chloroform). $^1$H NMR (300 MHz, DMSO) δ 11.06 (s, 1H), 8.12 (s, 1H), 7.49 (s, 1H), 6.94 (s, 2H), 5.86 (s, 1H), 5.44 (t, J=4.2 Hz, 1H), 5.02 (s, 1H), 4.56 (dd, J=11.3, 6.9 Hz, 1H), 4.40 (dd, J=11.3, 4.2 Hz, 1H), 4.16-3.98 (m, 1H), 2.09-1.94 (m, 9H), 1.48-1.14 (m, 9H); MS (ES+) 492.1 (M+1); (ES−) 526.4 (M+Cl); Analysis: Calculated for $C_{22}H_{29}N_5O_8.1.25H_2O$: C, 51.41; H, 6.18; N, 13.62. Found: C, 51.24; H, 5.92; N, 13.33.

Step-6:

Batch 1. To (2R,3R,4S,5S)-2-(acetoxymethyl)-5-(4-amino-5H-pyrrolo[3,2-d]pyrimidin-7-yl)-1-(tert-butoxycarbonyl)pyrrolidine-3,4-diyl diacetate (1-6) (81.5 g, 165.8 mmol), were added anhydrous methanol (370 mL) followed by the addition of NaOMe (sodium methoxide, 25 wt. % solution in methanol, 4.49 g, 20.76 mmol) at room temperature. The reaction mixture was stirred at room temperature until TLC (chloroform:methanol 9:1) shows that all the starting material had reacted.

Batch 2. To (2R,3R,4S,5S)-2-(acetoxymethyl)-5-(4-amino-5H-pyrrolo[3,2-d]pyrimidin-7-yl)-1-(tert-butoxycarbonyl)pyrrolidine-3,4-diyl diacetate (1-6) (117.8 g, 239.6 mmol), were added anhydrous methanol (530 mL) followed by the addition of NaOMe (sodium methoxide, 25 wt. % solution in methanol, 6.58 g, 30.45 mmol) at room temperature. The reaction mixture was stirred at room temperature until TLC (chloroform:methanol 9:1) shows that all the starting material had reacted;

Batch 3. —To (2R,3R,4S,5S)-2-(acetoxymethyl)-5-(4-amino-5H-pyrrolo[3,2-d]pyrimidin-7-yl)-1-(tert- butoxycarbonyl)pyrrolidine-3,4-diyl diacetate (1-6) (129.5 g, 263.5 mmol) were added anhydrous methanol (584 mL) followed by the addition of NaOMe (sodium methoxide, 25 wt. % solution in methanol, 6.99 g, 32.35 mmol) at room temperature. The reaction mixture was stirred at room temperature until TLC (chloroform:methanol 9:1) shows that all the starting material had reacted (7-8 hours).

The above solutions were concentrated (water bath 65-75° C.) to furnish (2S,3S,4R,5R)-tert-butyl 2-(4-amino-5H-pyrrolo[3,2-d]pyrimidin-7-yl)-3,4-dihydroxy-5-(hydroxymethyl)pyrrolidine-1-carboxylate (1-7) which was pure enough to be used as is for next step. An analytical sample was prepared by purification of the mixture using flash column chromatography (0-10% methanol in chloroform). $^1$H NMR (300 MHz, DMSO) δ 10.77 (s, 1H), 8.01 (s, 1H), 7.40 (s, 1H), 6.82 (s, 3H), 5.04-4.91 (m, 1H), 4.87-4.74 (m, 1H), 4.56-4.35 (m, 2H), 4.04-3.90 (m, 2H), 3.72-3.63 (m, 1H), 3.59-3.41 (m, 1H), 1.15 (2s, 9H); MS (ES+) 366.1 (M+1); (ES−) 400.3 (M+Cl); Analysis: Calculated for $C_{16}H_{23}N_5O_5 \cdot 0.25H_2O$: C, 51.33; H, 6.46; N, 18.71. Found: C, 51.04; H, 6.43; N, 18.48.

Step-7:

(2S,3S,4R,5R)-tert-butyl 2-(4-amino-5H-pyrrolo[3,2-d]pyrimidin-7-yl)-3,4-dihydroxy-5-(hydroxymethyl)pyrrolidine-1-carboxylate (1-7) were treated as follows in three batches.

Batch 1. (1-7) was dissolved in aq. HCl (118 mL of conc. HCl and 293 mL of water);

Batch 2. (1-7) was dissolved in aq. HCl (169 mL of conc. HCl and 421 mL of water).

Batch 3. (1-7) was dissolved in aq. HCl (186 mL of conc. HCl and 468 mL of water).

The reaction mixtures were stirred at room temperature for 30 min (strong evolution of $CO_2$ gas) and then each batch was concentrated in vacuum to dryness (80-90° C.). Batches 2 and 3 were pooled to give 226 g of damp clear yellow product. Batch 1 gave 91.4 of a dark grayish product. The crystallization was done as follows: For batches 2&3 wet product: 226 mL of water were added to the product then heated to 50° C. at which point hot ethanol was slowly added until crystallization started. The mixture was kept at 50° C. for 10 minutes then allowed to reach 25° C. with strong stirring before filtration to give light yellow colored powder of (2S,3S,4R,5R)-2-(4-amino-5H-pyrrolo[3,2-d]pyrimidin-7-yl)-5-(hydroxymethyl)pyrrolidine-3,4-diol (1) (88 g). Batch one was purified the same way to give 33.0 g light grayish colored product. The total yield is 121.0 g after drying at 55° C. at high vacuum. The mother liquor from the recrystallization of batches 1 and 2 was reprocessed to give 15.0 g of light yellowish powder product (1). $^1$H NMR (300 MHz, DMSO) δ 14.60 (s, 1H), 13.25 (s, 1H), 10.23 (s, 1H), 9.13 (s, 2H), 8.84 (s, 1H), 8.63 (s, 1H), 8.11 (d, J=3.1 Hz, 1H), 5.55 (s, 2H), 4.78 (d, J=4.4 Hz, 1H), 4.44 (dd, J=8.8, 5.0 Hz, 1H), 4.14-4.02 (m, 1H), 3.73 (d, J=5.1 Hz, 2H), 3.52 (s, 1H); $^1$H NMR (300 MHz, $D_2O$) δ 8.33 (s, 1H), 7.94 (s, 1H), 4.90 (d, J=8.9 Hz, 1H), 4.65 (s, 1H), 4.37 (dd, J=4.8, 3.4 Hz, 1H), 3.89 (s, 1H), 3.88 (s, 1H), 3.81 (dd, J=8.1, 4.5 Hz, 1H); MS (ES+) 266.3 (M+1); Optical rotation −52.69; ($H_2O$, C=1.15); MP: 238° C.; Analysis: Calcd for $C_{11}H_{15}N_5O_3 \cdot 2HCl \cdot 0.25H_2O$: C, 38.55; H, 5.15; Cl, 20.44; N, 20.69. Found: C, 38.67; H, 5.05; Cl, 20.45; N, 20.42.

Example 3

Phosphorylation of Compound 1 (Formula I, Wherein A=NH$_2$ and B=H) and DNA/RNA Incorporation Studies Human hepatocellular carcinoma (Huh-7) cells were incubated with $^3$H-compound 1 for 24 hrs, followed by methanol extraction and HPLC analysis using SAX column and radioactive detector. FIG. 1 shows the phosphorylation of compound 1 in Huh-7 cells, indicating efficient phosphorylation in cells.

Figure 2:
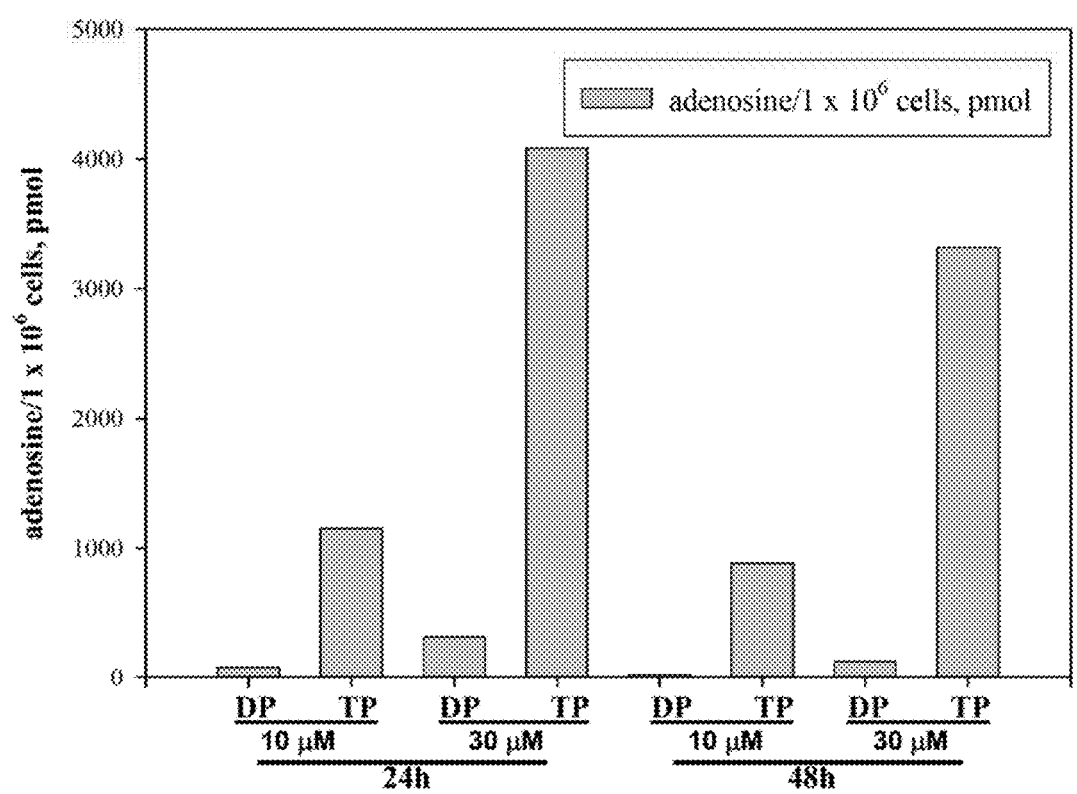
FIG. 2 shows phosphorylation of $^3$H adenosine in Huh-7 cells.
Figure 3:
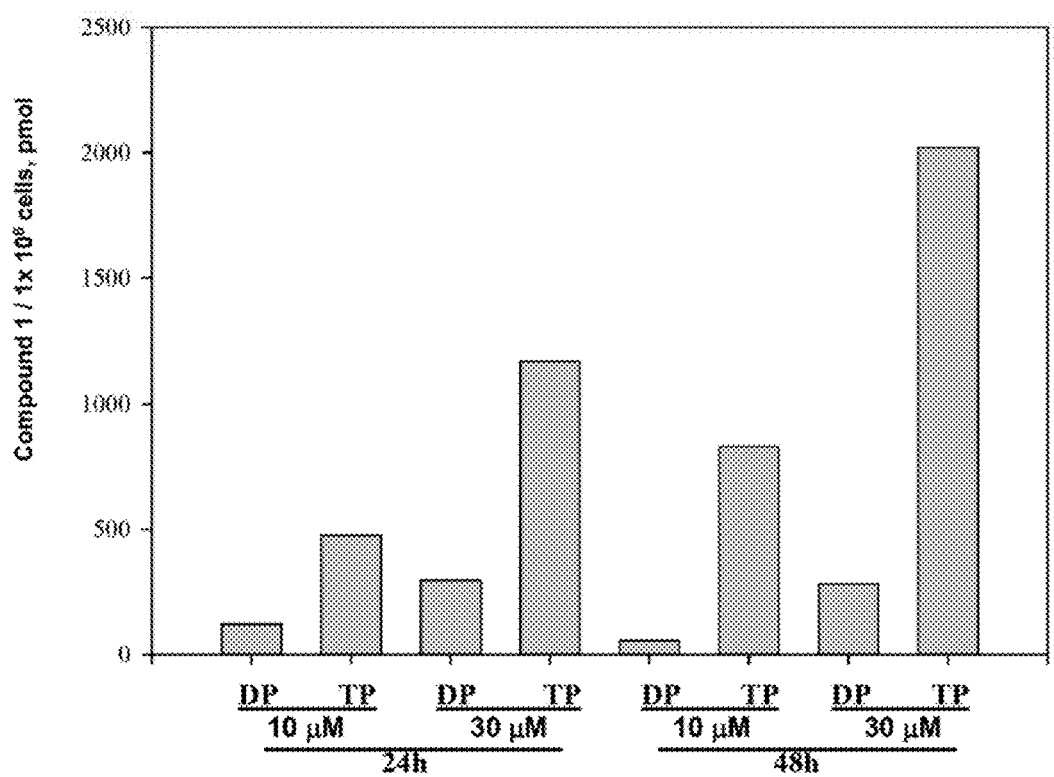
FIG. 3 shows phosphorylation of $^3$H compound 1 in Huh-7 cells.
Figure 4:
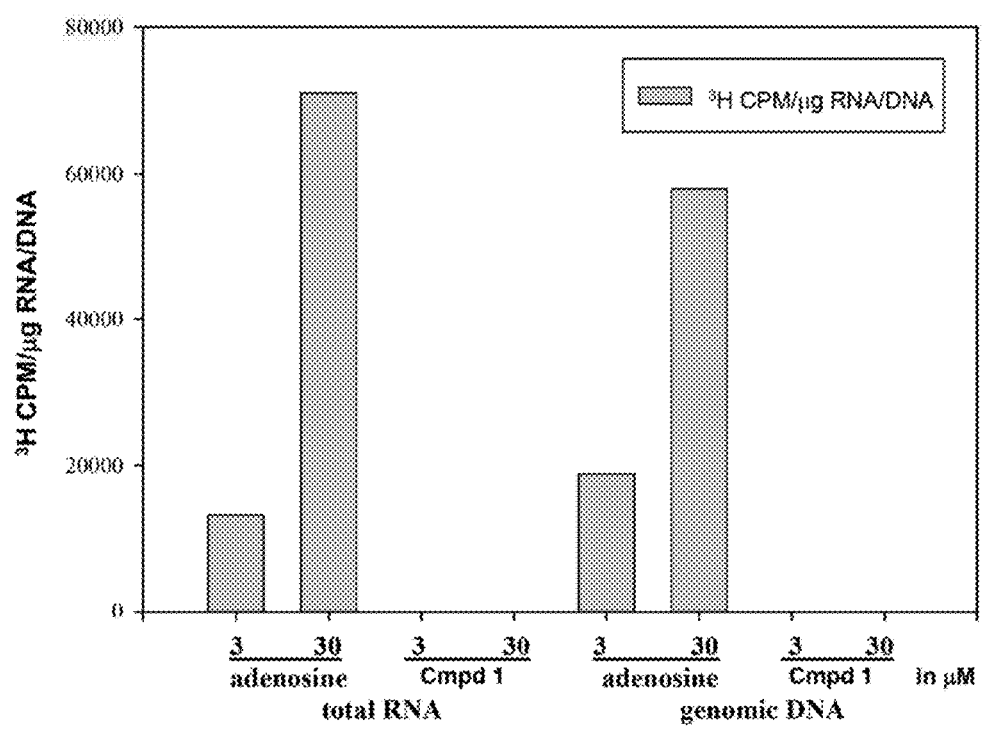
FIG. 4 shows total RNA and genomic DNA incorporation of $^3$H compound 1 and $^3$H adenosine in Huh-7 cells after 24 h.

FIGS. 2-4 show that compound 1 is phosphorylated but not incorporated into mammalian RNA or DNA (DP designates diphosphate and TP designates triphosphate). FIG. 2 shows phosphorylation of adenosine in Huh-7 cells. FIG. 3 shows phosphorylation of compound 1 in Huh-7 cells. FIG. 4 shows total RNA and genomic DNA incorporation of compound 1 and adenosine in Huh-7 cells.

Example 4

Effects of Viral RNA Polymerase Inhibitor (Formula I, Wherein A=NH$_2$ and B=H: Compound 1) on Replication of Measles Virus in African Green Monkey Kidney Cells Materials and Methods: Vero 76 cells (African green monkey kidney cells) were obtained from the American Type culture collection (ATCC, Manassas, Va.). The cells were routinely passed in minimal essential medium (MEM with 0.15% NaHCO$_3$; Hyclone Laboratories, Logan, Utah, USA) supplemented with 5% fetal bovine serum (FBS, Hyclone). When evaluating compounds, the serum was reduced to a final concentration of 2.5%, and gentamicin is added to the test medium to a final concentration of 50 μg/mL. Measles virus (MV), strain Chicago, was obtained from the Centers for Disease Control (Atlanta, Ga.).

Antiviral Testing Procedures:

Cytopathic Effect inhibition Assay (Visual Assay)

Cells were seeded to 96-well flat-bottomed tissue culture plates (Corning Glass Works, Corning, N.Y.), 0.2 mL/well, at the proper cell concentration, and incubated overnight at 37° C. in order to establish a cell monolayer. When the monolayer was established, the growth medium was decanted and the various dilutions of test compound were added to each well (3 wells/dilution, 0.1 mL/well). Compound diluent medium was added to cell and virus control wells (0.1 mL/well). Virus, diluted in test medium, was added to compound test wells (3 wells/dilution of compound) and to virus control wells (6 wells) at 0.1 mL/well. Virus (viral MOI=0.001) was added approximately 5 min after compound. Test medium without virus was added to all toxicity control wells (2 wells/dilution of each test compound) and to cell control wells (6 wells) at 0.1 mL/well. The plates were incubated at 37° C. in a humidified incubator with 5% CO$_2$, 95% air atmosphere until virus control wells had adequate cytopathic effect (CPE) readings (80-100% cell destruction). This was achieved from 4-11 days after virus exposure to cells, depending on the virus. Cells were then examined microscopically for CPE, this being scored from 0 (normal cells) to 4 (maximal, 100%, CPE). The cells in the toxicity control wells were observed microscopically for morphologic changes attributed to cytotoxicity. This cytotoxicity (cell destruction and/or morphology change) was also graded at 100% toxicity, 80% cytotoxicity, 60% cytotoxicity, 40% cytotoxicity, 20% cytotoxicity, and 0 (normal cells). The 50% effective dose (EC50) and 50% cytotoxic dose (IC50) were calculated by regression analysis of the virus CPE data and the toxicity control data, respectively. The selective index (SI) for each compound tested was calculated using the formula: SI=CC50÷EC50.

Neutral Red (NR) Uptake Assay of CPE Inhibition

NR red was chosen as the dye quantitation method for evaluating antiviral drugs based on the findings of Smee et al (*J. Virol. Methods* 2002, 106: 71-79; herein incorporated by reference in its entirety). This assay was done on the same CPE inhibition test plates described above to verify the inhibitory activity and the cytotoxicity observed by visual observation. The NR assay was performed using a modified method of Cavenaugh et al. (*Invest. New Drugs* 1990, 8:347-354; herein incorporated by reference in its entirety) as described by Barnard et al. (*Antiviral Chem. Chemother.* 2001, 12:220-231; herein incorporated by reference in its entirety). Briefly, medium was removed from each well of a plate scored for CPE from a CPE inhibition assay, 0.034% NR was added to each well of the plate and the plate incubated for 2 hr at 37° C. in the dark. The NR solution was then removed from the wells. After rinsing (sometimes cells slough from the plate causing erroneous low up of neutral red) and aspirating to dryness, the remaining dye was extracted for 30 min at room temperature in the dark from the cells using absolute ethanol buffered with Sörenson citrate buffer. Absorbances at 540 nm/405 nm are read with a microplate reader (Opsys MR™, Dynex Technologies, Chantilly, Va., USA). Absorbance values were expressed as percents of untreated controls and EC50, CC50 and SI values were calculated as described above.

Virus Yield Reduction Assay

Virus yield reduction assays were performed using the cell culture 50% infectious dose (CCID50) assay essentially as described previously (*Antimicrob. Agents Chemother.* 1992, 3:1837-1842; herein incorporated by reference in its entirety). Briefly, supernatants from each well were serially diluted in triplicate wells of 96-well plates containing Vero-76 cells. Plates were incubated for 6 days and then checked for virus-induced CPE. Quantitation of virus yield titers was by the end point method of Reed and Muench (*Am. J. Hyg.* 1938, 27:493-498; herein incorporated by reference in its entirety). The EC90 value was calculated using linear regression to estimate the concentration necessary to inhibit virus yield by 90% or a one log 10 decrease in virus titer.

Results and Discussion

Measles virus was potently inhibited by compound 1 (Table 1). EC50 values against the measles virus were 0.6 and 1.4 μg/mL by visual assay and NR assay, respectively. The compound did not have any cytotoxicity in either the visual or NR assays (IC50>100). Therefore, the selective indices by both assays suggested that compound 1 was highly active against measles virus (MV). The potent inhibitory activity against MV was confirmed by a virus yield reduction assay with an EC90=0.36 μg/mL, representing a one log 10 drop in virus produced in infected cells.

Conclusions

Compound 1 demonstrated potent and selective inhibitory activity. By virus yield reduction assay, compound 1 was also a potent inhibitor of MV (EC90=0.37 μg/mL). Thus, compound 1 has been found to be a potent inhibitor of many RNA viruses and suggests that compound 1 warrants further in vitro and in vivo evaluation as a broad-spectrum inhibitor of selected RNA viruses.

Example 5

Effects of Viral RNA Polymerase Inhibitor (Formula I, Wherein A=$NH_2$ and B=H: Compound 1) on Replication of Various RNA Viruses Materials and Methods Cells and Virus African green monkey kidney cells (MA-104) were obtained from Whitaker MA Bioproducts, Walkersville, Md., USA). All Vero cells (African green monkey kidney cells, human carcinoma of the larynx cells (A-549), and Madin-Darby canine kidney cells were obtained from the American Type Culture Collection (ATCC, Manassas, Va.). A-549 cells were cultured in Dulbecco's minimal essential medium (DMEM) supplemented with 0.15% $NaHCO_3$ (Hyclone Laboratories, Logan, Utah, USA) and with 10% fetal bovine serum (FBS, Hyclone). The remaining cells were routinely passed in minimal essential medium (MEM with 0.15% $NaHCO_3$; Hyclone Laboratories, Logan, Utah, USA) supplemented with 5% fetal bovine serum (FBS, Hyclone).

When evaluating compounds, the serum was reduced to a final concentration of 2.5%, and gentamicin is added to the test medium to a final concentration of 50 μg/mL. Test medium for influenza assays consisted of MEM without serum, 0.18% $NaHCO_3$, 20 μg trypsin/mL, 2.0 μg EDTA/mL, and 50 μg gentamicin/mL.

For evaluation of toxicity in actively growing cells, cytotoxicity was evaluated by determining the total number of cells as reflected by a NR uptake assay after a 3-day exposure to several concentrations of compound. To quantitate cell growth at 72 h in the presence or absence of drug, plates were seeded with $1\times10^3$ MDCK cells, and after 4 h (allowed all cells to attach plate wells) were exposed to selected concentrations of drug in MEM or MEM. After 72 h the plates were treated as described above for the NR assay. Absorbance values were expressed as percent of untreated controls and CC50 values were calculated by regression analysis.

Dengue virus 2 (DV-2), strain New Guinea C, Respiratory syncytial virus (RSV) A2, Rhinovirus 2 (RV-2), strain HGP, Tacaribe (TCV), strain TRVL 11573, Venezuelan equine encephalitis virus (VEE), and Yellow fever virus (YFV), strain 17D were all purchased from American Type Culture Collection (ATCC; Manassas, Va.). All influenza viruses, Measles virus (MV), strain Chicago, SARS corona virus (SARS-CoV), strain Urbani, and West Nile virus (WNV), prototypic New York 1999 isolate designated strain 996625, were obtained from the Centers for Disease Control (Atlanta, Ga.). Punta Toro virus (PTV), Adames strain, was obtained form Dr. Dominique Pifat of the U.S. Army Medical Research Institute for Infectious Diseases, Ft. Detrick (Frederick, Md.). The Rift Valley fever virus (RVFV) vaccine strain, MP-12, and the Junin virus (JUNV) vaccine strain, Candid 1, were kindly provided by Dr. Robert Tesh (World Reference Center for Emerging and Viruses and Arboviruses, University of Texas Medical Branch, Galveston, Tex.). Pichinde virus (PICV), strain An 4763, was provided by Dr. David Gangemi (Clemson University, Clemson, S.C.). Parainfluenza virus type 3 (PIV-3), strain 14702/5/95, was obtained from Jacquelin Boivin (Hospitale St. Justin, Montreal, Canada). Adenovirus (AV-1) type 1, strain Chicago/95, was isolated from the tracheal washings of a pediatric patient and was provided by M. F. Smaron (Department of Medicine, University of Chicago, Chicago Ill.).

Antiviral Testing Procedure

Cytopathic Effect inhibition Assay (Visual Assay)

Cells were seeded to 96-well flat-bottomed tissue culture plates (Corning Glass Works, Corning, N.Y.), 0.2 mL/well, at the proper cell concentration, and incubated overnight at 37° C. in order to establish a cell monolayer. When the monolayer was established, the growth medium was decanted and the various dilutions of test compound were added to each well (3 wells/dilution, 0.1 mL/well). Compound diluent medium was added to cell and virus control wells (0.1 mL/well). Virus, diluted in test medium, was added to compound test wells (3 wells/dilution of compound) and to virus control wells (6 wells) at 0.1 mL/well. Virus (viral MOI=0.001) was added approximately 5 min after compound. Test medium without virus was added to all toxicity control wells (2 wells/dilution of each test compound) and to cell control wells (6 wells) at 0.1 mL/well. The plates were incubated at 37° C. in a humidified incubator with 5% CO$_2$, 95% air atmosphere until virus control wells had adequate cytopathic effect (CPE) readings (80-100% cell destruction). This was achieved from 4-11 days after virus exposure to cells, depending on the virus. Cells were then examined microscopically for CPE, this being scored from 0 (normal cells) to 4 (maximal, 100%, CPE). The cells in the toxicity control wells were observed microscopically for morphologic changes attributed to cytotoxicity. This cytotoxicity (cell destruction and/or morphology change) was also graded at 100% toxicity, 80% cytotoxicity), 60% cytotoxicity, 40% cytotoxicity, 20% cytotoxicity, and 0 (normal cells). The 50% effective dose (EC50) and 50% cytotoxic dose (IC50) were calculated by regression analysis of the virus CPE data and the toxicity control data, respectively. The selective index (SI) for each compound tested was calculated using the formula: SI=CC50 EC50.

Neutral Red (NR) Uptake Assay of CPE Inhibition and Compound Cytotoxicity

NR red was chosen as the dye quantitation method for evaluating antiviral drugs based on the findings of Smee et al (supra). This assay was done on the same CPE inhibition test plates described above to verify the inhibitory activity and the cytotoxicity observed by visual observation. The NR assay was performed using a modified method of Cavenaugh et al. (supra) as described by Barnard et al. (supra). Briefly, medium was removed from each well of a plate scored for CPE from a CPE inhibition assay, 0.034% NR was added to each well of the plate and the plate incubated for 2 hr at 37° C. in the dark. The NR solution was then removed from the wells. After rinsing (sometimes cells slough from the plate causing erroneous low up of neutral red) and aspirating to dryness, the remaining dye was extracted for 30 min at room temperature in the dark from the cells using absolute ethanol buffered with Sörenson citrate buffer. Absorbances at 540 nm/405 nm are read with a microplate reader (Opsys MR™, Dynex Technologies, Chantilly, Va., USA). Absorbance values were expressed as percents of untreated controls and EC50, CC50 and SI values were calculated as described above.

TABLE 1

Effects of a polymerase inhibitor (compound 1) on the replication of various viruses.

| Virus | Visual CPE Assay (μg/mL) | | | Neutral Red Uptake Assay (μg/mL) | | |
|---|---|---|---|---|---|---|
| | EC50 | IC50 | SI | EC50 | IC50 | SI |
| Adenovirus type 165089/Chicago (A-549 cells) | 39 | >100 | >2.6 | 43 | >100 | >2.3 |
| Dengue 2 New Guinea C (Vero Cells) | 15 | 360 | 25 | 13 | 340 | 26 |
| Influenza A H1N1 CA/04/2009 (Pandemic H1N1) | 1.8 | 210 | 120 | 1.8 | 210 | 120 |
| Influenza A H3N2 Brisbane/10/2007 | 1.8 | 260 | 140 | 5.6 | 440 | 79 |
| Influenza A H5N1 VN/1203/2004 Hybrid (on H1N1 backbone) | 0.63 | >1000 | >1600 | 0.99 | 130 | 130 |
| Influenza B Florida | 1.8 | 530 | 290 | 1.8 | 50 | 38 |
| Junin Candid 1 (Vero Cells) | 29 | >520 | >17 | 16 | 240 | 14 |
| Measles | 0.6 | >100 | >180 | 1.4 | >100 | >71 |
| Parainfluenza 3 14702 (MA-104 cells) | 14 | 100 | 7.1 | 10 | 52 | 52 |
| Pichinde (Vero Cells) | 61 | >500 | >8.2 | 28 | 190 | 6.7 |
| Punta Toro A2 (Vero 76 Cells) | 310 | >500 | >1.6 | >250 | 250 | 0 |
| Respiratory Syncytial A2 (MA-104 cells) | >100 | >100 | 0 | >100 | >100 | 0 |
| Rhinovirus 2 HGP (HeLa Ohio-1 cells) | 57 | >100 | >1.8 | 56 | >100 | >1.8 |
| Rift Valley Fever MP-12 (Vero 76 Cells) | 75 | 680 | 9.1 | 64 | 420 | 6.6 |
| SARS-CoV Urbani (Vero 76 cells) | 14 | >100 | >7.1 | 16 | >100 | >6.3 |
| Tacaribe TRVL 11573 (Vero Cells) | 29 | 320 | 4.2 | 2 | 200 | 2 |
| Venezuelan Equine Encephalitis TC83 (Vero 76 Cells) | 280 | 610 | 2.2 | 170 | 230 | 1.2 |
| West Nile (Vero Cells) | >100 | >100 | 0 | 36 | >100 | 2.8 |
| Yellow Fever 17D (Vero 76 cells) | 8.3 | 360 | 43 | 8.3 | 320 | 38 |

Other viruses that were considered significantly inhibited by compound 1 (SI>10) were DV-2 (EC50=15, 13 μg/mL), JUNV (EC50=29, 16 μg/mL), YFV (EC50=8.3, 8.3 μg/mL) (Table 1). The following viruses were slightly inhibited by compound 1 (10<SI>3): PIV-3 (EC50=7.1, 10 μg/mL), SARS-CoV (EC50=14, 16 μg/mL), PICV (EC50=61, 28 μg/mL), and RVFV (EC50=75, 64 μg/mL). Compound 1 was tested against a subset of influenza viral strains (Table 2), and exhibited broad spectrum anti-influenza activity against multiple strains.

TABLE 2

Broad Spectrum Anti-influenza activity of compound 1.

| Virus | EC50 (µg/mL) |
|---|---|
| A/CA/04/2009 (Pandemic H1N1) | 1.8 |
| A/Brisbane/10/2007 (H3N2) | 5.6 |
| A/VN/1203/2004 (H5N1) | 0.99 |
| B/Florida | 1.8 |
| A/CA/27/2007 (H1N1) | 0.66 |
| A/NJ/15/2007 (H1N1-H274Y) | 1.39 |
| A/Vic/3/75 (H3N2) | 4.0 |

Conclusions

Compound 1 demonstrated potent activity against all the influenza viruses tested. Compound 1 was found to be a potent inhibitor of influenza virus replication and suggests that compound 1 is effective as a broad-spectrum inhibitor of selected RNA viruses, including all influenza viruses.

Example 6

In Vitro Antiviral Activity of Compound 1

Antiviral activity of Compound 1 was assessed in vitro in several viruses for antiviral activity. EC50 values ranged from about 10 µg/mL to about >300 µg/mL against Marburg (filoviridae), Junin Candid 1 (arenaviridae), Pichinde (arenaviridae), Chikungunya 181/25 (togaviridae) and Vaccinia NYCBH (poxviridae).

Example 7

Synergistic Antiviral Activity of Compound 1 and Neuraminidase Inhibitor in MDCK Cells Madin Darby Canine Kidney (MDCK) cells were infected with influenza virus H3N2 (A/Victoria/3/75) virus and treated with various combinations of compound 1 and peramivir for 72 hrs. Cytopathic effect was determined using neutral red dye uptake assay. The data is shown in table 3.

TABLE 3

Percent Inhibition of Cytopathic Effect in Influenza Infected Cells.

| | Peramivir | | |
|---|---|---|---|
| Compound 1 | 0.0 µM | 0.0 µM | 0.0 µM |
| 0.0 µM | 0 | 3.6 ± 9 | 10.8 ± 11 |
| 1.8 µM | 1.6 ± 6.1 | 22.7 ± 6.1 | 21.5 ± 4.6 |
| 7.8 µM | 25.8 ± 4.8 | 50.4 ± 7.9 | 70.3 ± 4.9 |

Figure 5:
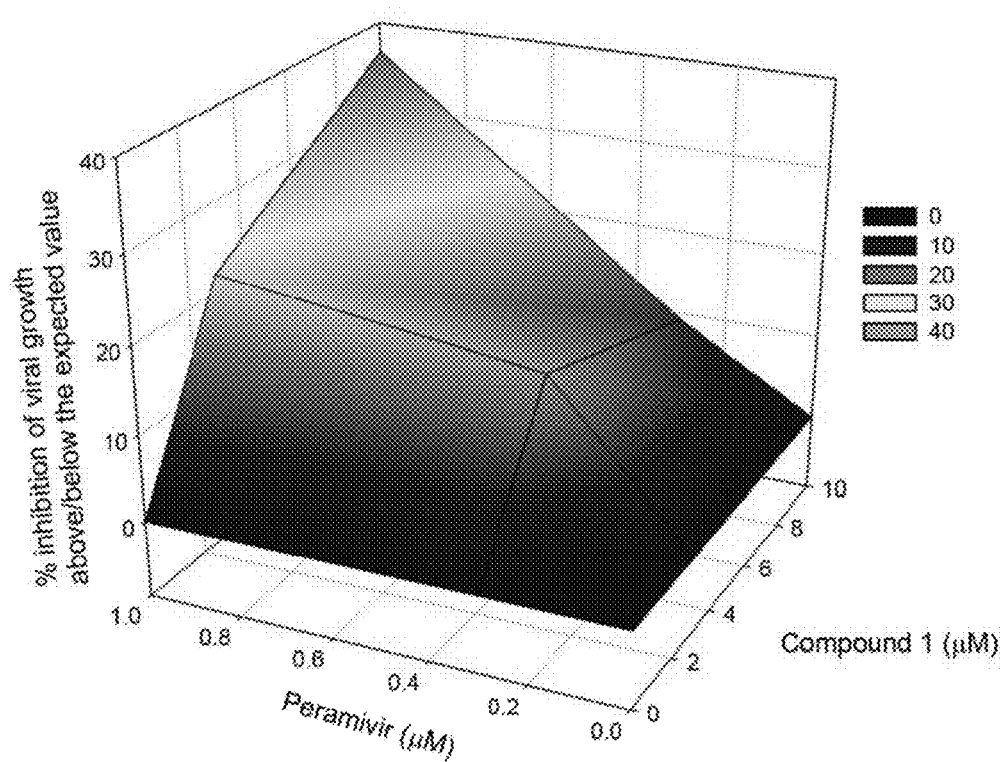
FIG. 5 shows the combination effects of compound 1 and peramivir (a neuraminidase inhibitor) on influenza in vitro.

The experimental data were evaluated by the three dimensional analysis using Mac Synergy II™ software program (Prichard and Shipman, 1990; herein incorporated by reference in its entirety). The software calculates the theoretical additive interactions from the dose-response curves of the individual drugs. The calculated additive surface, which represents the predicted additive interactions, is then subtracted from the experimental surface to reveal regions of greater (synergy) or less (antagonism)-than-expected interactions. Combination of peramivir and compound 1 in cell culture studies demonstrated a synergistic antiviral effect with a volume of synergy equal to 92 uM$^2$ unit % (FIG. 5).

Example 8

Efficacy of Compound 1 Intramuscular Injection (IM) in Murine Influenza Model

Figure 6:
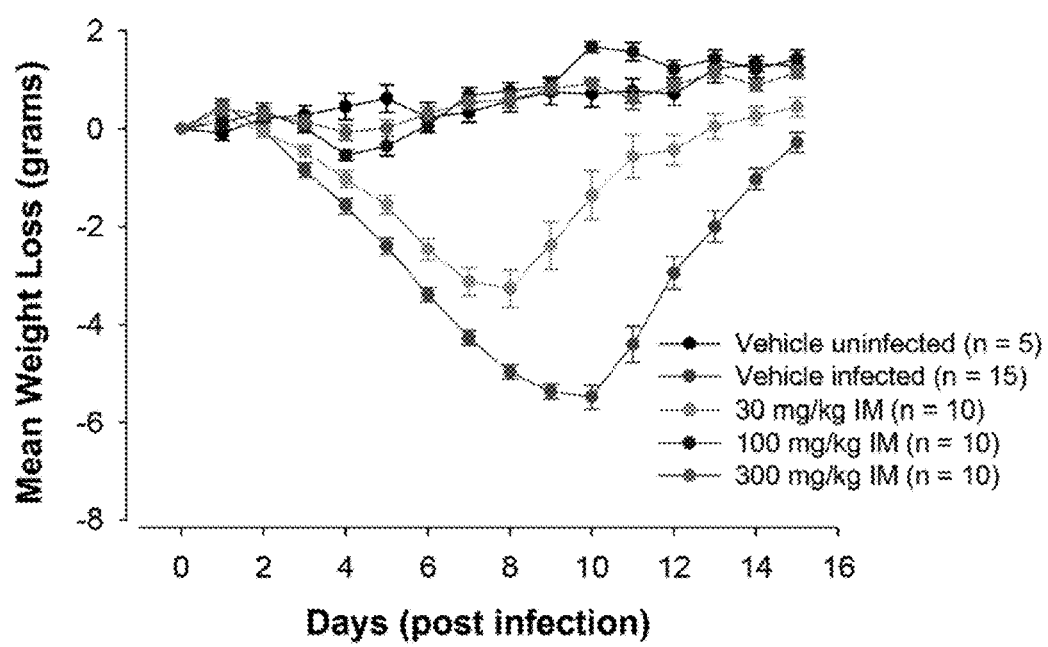
FIG. 6 shows the effect of compound 1 (intramuscular) on weight loss in mice infected with H3N2 A/Victoria/3/75 influenza virus.

Balb/C mice between 6-8 weeks old were adapted to H3N2 virus (A/Victoria/3/75). Doses of 0, 30, 100, and 300 mg/kg/d qd were given by intramuscular (IM) injection for 5 days starting 1 hr prior to infection. N=50 animals. All animals were followed for 16 days. Endpoints included lethality, mean days to death and weight loss. The effects are shown in FIG. 6.

Compound 1 (IM) in mouse influenza model virus results are also shown in table 4. Compound 1 given IM improves the survival and weight loss in mice infected with influenza virus.

TABLE 4

Compound 1 (IM) in mouse influenza model virus - H3N2 A/Vic/3/75

| Treatment | Dose Level (mg/kg/d) | Number of deaths | Mean day to death (Mean ± SEM) | Mean weight change (grams ± SEM) Day 8 |
|---|---|---|---|---|
| Vehicle, uninfected | 0 | 0 | >16 | 0.58 ± 0.23 |
| Vehicle, infected | 0 | 7/15 | 10.3 ± 0.3 | −4.98 ± 0.14 |
| compound 1 | 30 | 10/10* | >16 | −3.27 ± 0.37** |
| compound 1 | 100 | 10/10* | >16 | 0.78 ± 0.17** |
| compound 1 | 300 | 10/10* | >16 | 0.60 ± 0.17** |

*P < 0.001 compared to vehicle infected group (log rank test)
**P < 0.001 compared to vehicle infected group (t-test)

Example 9

Efficacy of Compound 1 Oral Administration in Murine Influenza Model

Figure 7:
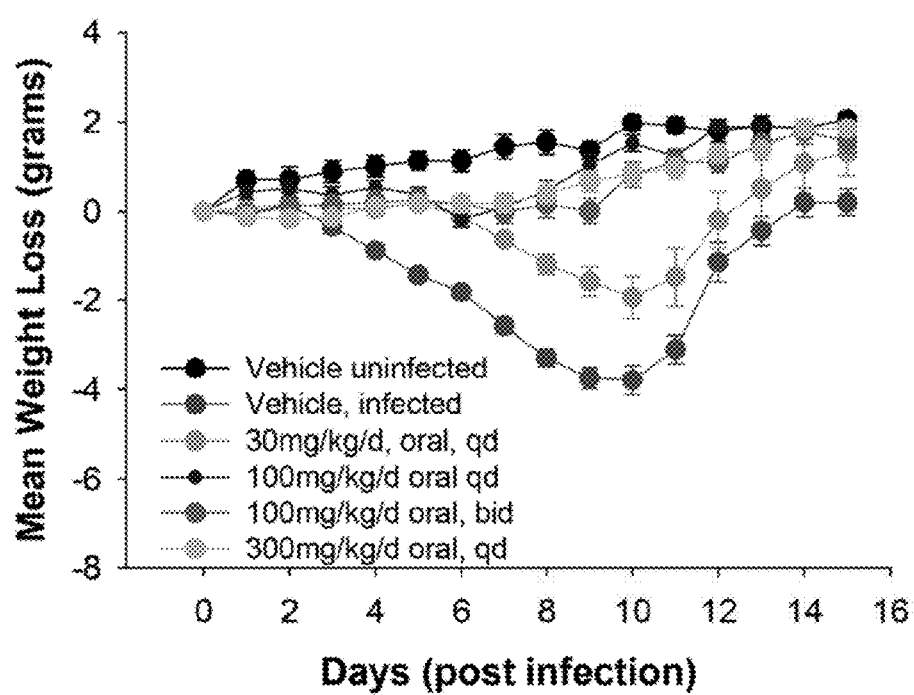
FIG. 7 shows the effect of compound 1 (oral) on weight loss in mice infected with H3N2 A/Victoria/3/75 influenza virus.

Balb/C mice between 6-8 weeks old were adapted to H3N2 virus (A/Victoria/3/75). Doses of 0, 30, 100, and 300 mg/kg/d qd and 100 mg/kg/d bid were given orally. N=60 animals. All animals were followed for 16 days. Endpoints included lethality, mean days to death and weight loss. The effects of orally administered compound 1 on weight loss in mice infected with H3N2 A/Vic/3/75 influenza virus are shown in FIG. 7.

Oral administration of compound 1 in mouse influenza model virus results are also shown in table 5. Compound 1 given orally improves the survival and weight loss in mice infected with influenza virus.

TABLE 5

Compound 1 (Oral) in mouse influenza model virus - H3N2 A/Vic/3/75

| Treatment | Dose Level (mg/kg/d) qd | Survival/ Total | Mean day to death (Mean ± SEM) | Mean weight change (grams ± SEM) Day 9 |
|---|---|---|---|---|
| Vehicle, uninfected | 0 | 0 | >16 | 1.36 ± 0.96 |

TABLE 5-continued

Compound 1 (Oral) in mouse influenza model virus - H3N2 A/Vic/3/75

| Treatment | Dose Level (mg/kg/d) qd | Survival/ Total | Mean day to death (Mean ± SEM) | Mean weight change (grams ± SEM) Day 9 |
|---|---|---|---|---|
| Vehicle, infected | 0 | 7/15 | 10.5 ± 0.3 | −3.74 ± 0.23 |
| compound 1 | 30 | 10/10* | >16 | −1.58 ± 0.32** |
| compound 1 | 100 | 10/10* | >16 | 1.03 ± 0.22** |
| compound 1 | 100 (bid) | 10/10* | >16 | 0.01 ± 0.27** |
| compound 1 | 300 | 10/10* | >16 | 0.66 ± 0.23** |

*P < 0.001 compared to vehicle infected group (log rank test)
**P < 0.001 compared to vehicle infected group (t-test)

Example 10

Pharmacokinetic Studies in Mice

Female Balb/c mice (N=30) were dosed orally with compound 1 at 100 mg/kg. Mice were bled through the retro orbital sinus at t=0.17, 0.5, 1.0, 3, 6, and 24 hrs (5 mice each per time point), centrifuged and plasma was stored at −80° C. Plasma drug levels were measured via LC/MS/MS analysis.

Mouse plasma levels for compound 1 after oral administration are shown in table 6.

TABLE 6

Compound 1 plasma levels in mice following oral administration

| Timepoint (hr) | Plasma drug levels (ng/mL) (Mean ± SEM) |
|---|---|
| 0.17 | 607.1 ± 61.0 |
| 0.5 | 910.0 ± 121.9 |
| 1 | 341.6 ± 121.9 |
| 3 | 89.7 ± 8.5 |
| 5 | 94.2 ± 6.4 |
| 24 | 50.5 ± 8.9 |

Example 11

Ebola Virus Mouse Prophylaxis Study

Compound 1 was administered i.p., i.m., and orally (300 mg/kg/day, BID) to 8-12 week old C57BI/6 mice (N=10 per group, 4 groups—one saline and 3 drug treated groups). Eight days of treatment starting 4 hr prior to infection. Mouse-adapted Ebola virus (Zaire) challenge was administered intraperitoneally. Mortality and weight were monitored for 14 days post-infection.

Figure 8:
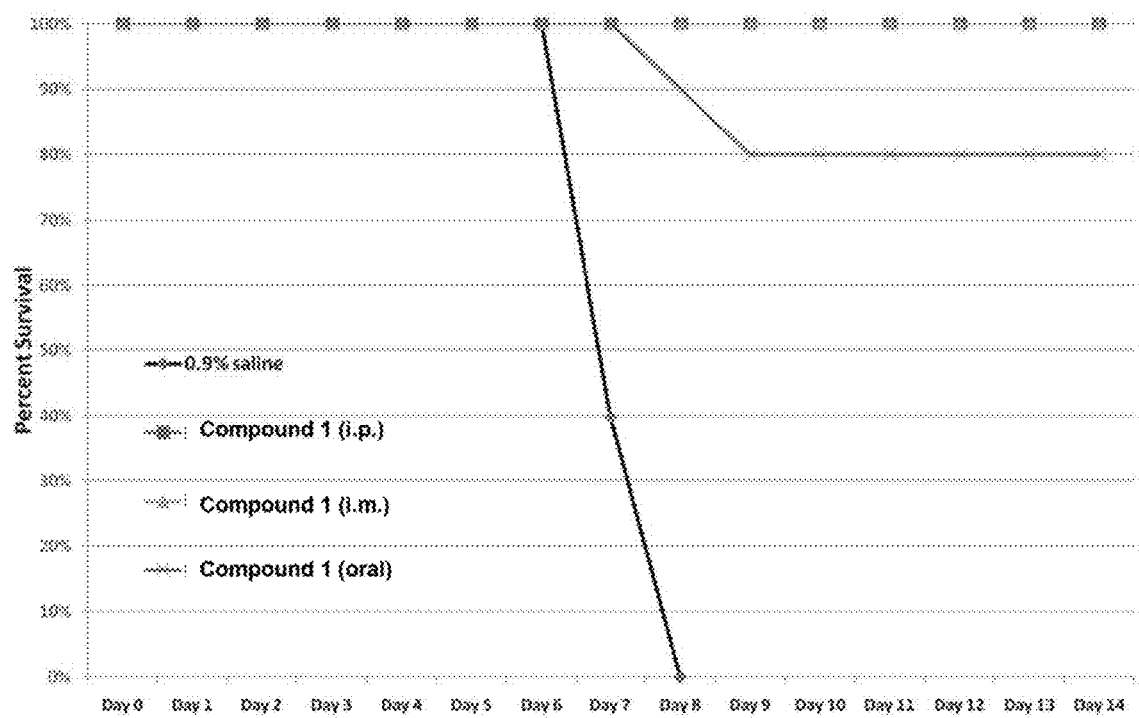
FIG. 8 shows the effect of compound 1 (intraperitoneal, intramuscular and oral) on survival of mice infected with Ebola virus.

Percent survival of mice is indicated in FIG. 8. Saline-treated mice infected with Ebola virus all died by day 8. All mice treated intraperitoneally or intramuscularly with compound 1 survived at study endpoint (day 14). Eighty percent of mice treated orally with compound 1 survived at study endpoint (day 14).

Figure 9:
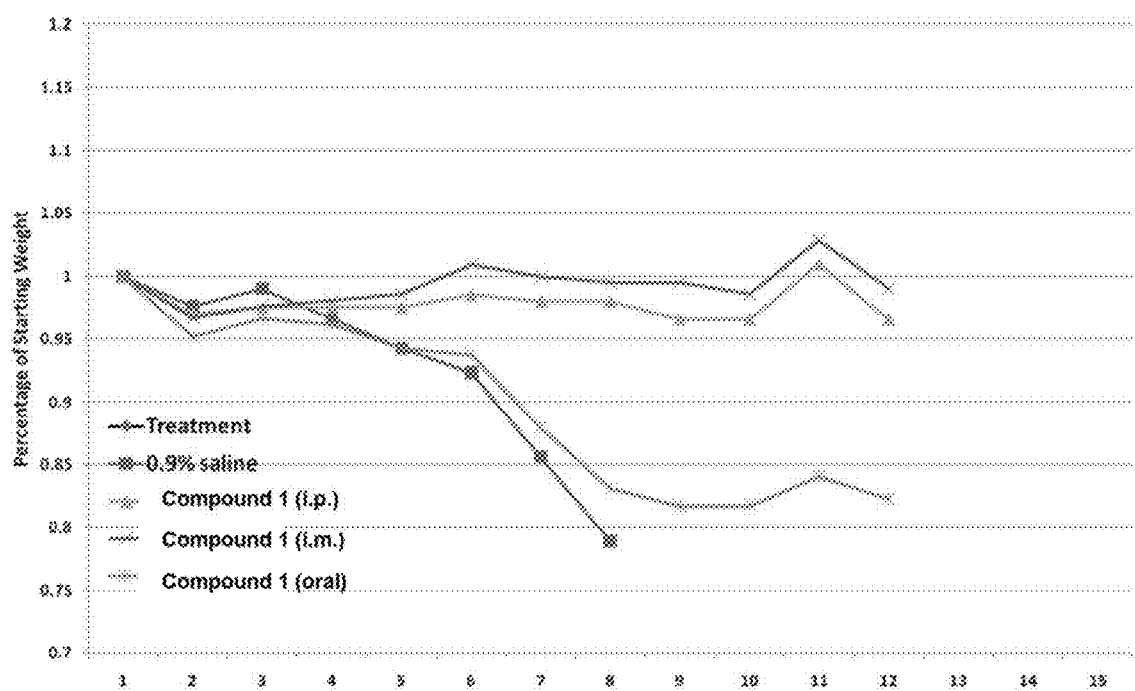
FIG. 9 shows the effect of compound 1 (intraperitoneal, intramuscular and oral) on weight loss in mice infected with Ebola virus.

Weight change of mice is indicated in FIG. 9. Saline-treated mice infected with Ebola virus exhibited overall weight loss until day 8 (all control mice were dead by day 8). Mice treated intraperitoneally or intramuscularly with compound 1 retained greater than 95% of starting weight at day 12. Mice treated orally with compound 1 retained greater than 80% of starting weight at day 12. All drug treated mice continued to gain weight after day 12.

Example 12

Ebola Virus Mouse Prophylaxis Study

Compound 1 was administered i.m. and orally to 8-12 week old C57BI/6 mice. The study subjects were divided into 6 groups (N=10 per group). Group 1 was a saline control, group 2 was dosed with 150 mg/kg compound 1 (PO, BID); group 3 was dosed with 250 mg/kg compound 1 (PO, BID); group 4 was dosed with 150 mg/kg compound 1 (IM, BID). Group 5 was uninfected mice treated with saline (PO, BID), and group 6 was uninfected mice treated with 250 mg/kg compound 1 (PO, BID). Treatment was for nine days, starting 4 hr prior to infection. Mouse-adapted Ebola virus (Zaire) challenge was administered intraperitoneally 1,000 pfu). Mortality and weight were monitored for 14 days post-infection.

Figure 10:
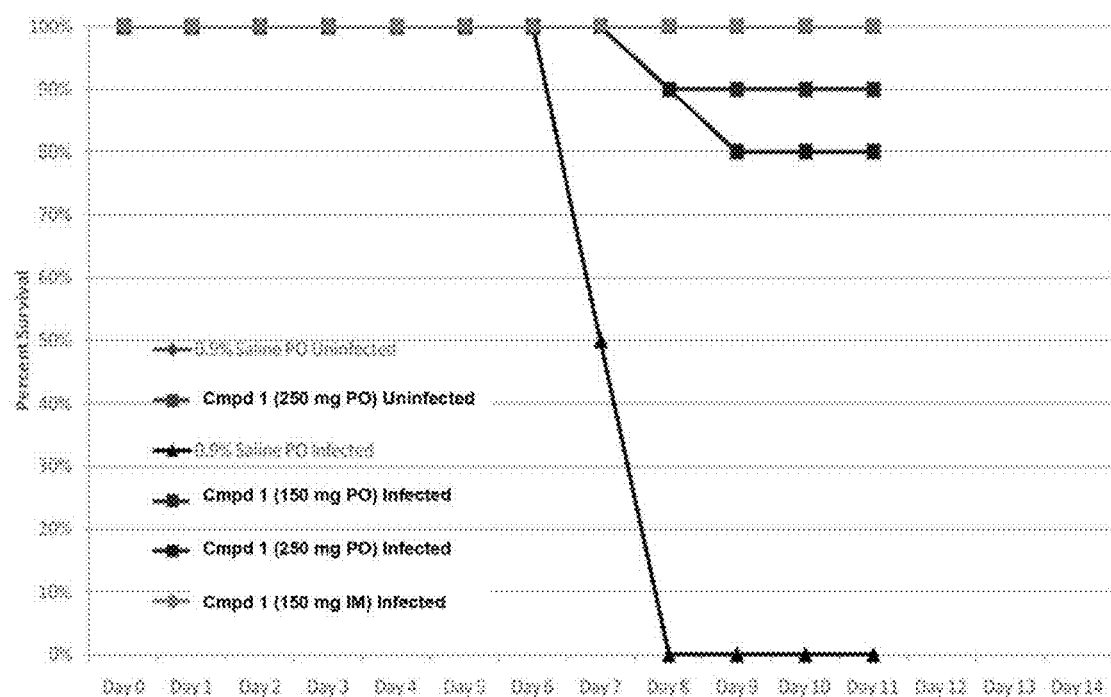
FIG. 10 shows the effect of compound 1 (intramuscular and oral) on survival of mice infected with Ebola virus.

Percent survival of mice is indicated in FIG. 10. Saline-treated mice infected with Ebola virus all died by day 8. All mice treated intramuscularly with compound 1 survived at study endpoint, indicating that the IM dosage of compound 1 was completely protective. Eighty percent or greater of mice treated orally with compound 1 survived at study endpoint.

Figure 11:
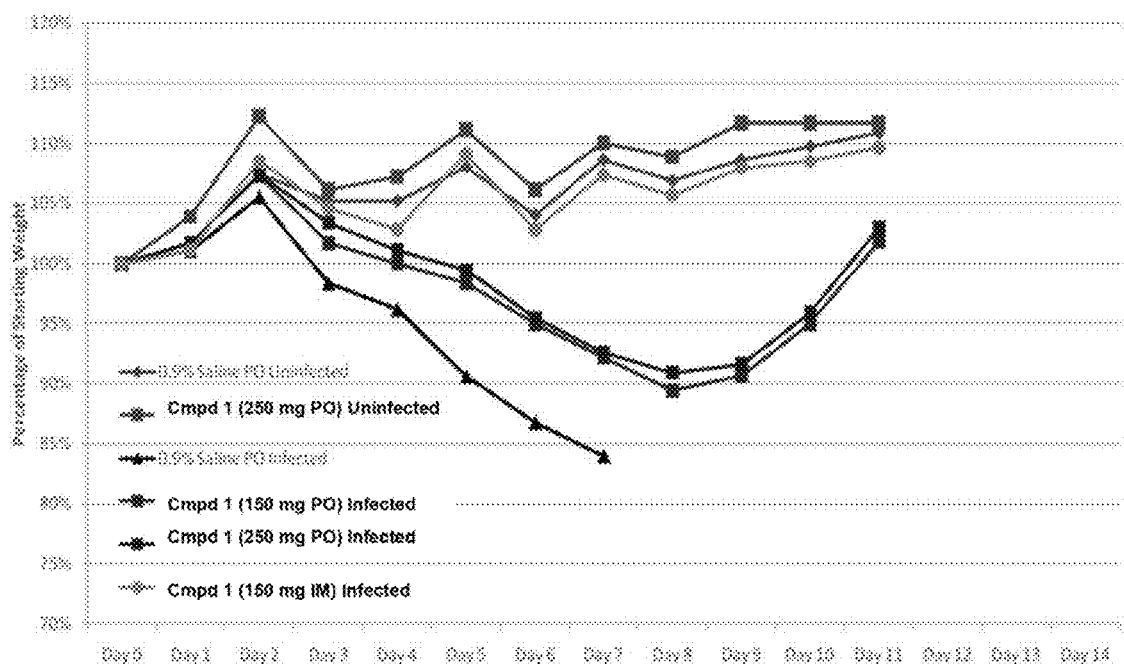
FIG. 11 shows the effect of compound 1 (intramuscular and oral) on weight loss in mice infected with Ebola virus.

Weight change of mice is indicated in FIG. 11. Saline-treated mice infected with Ebola virus exhibited overall weight loss until day 7 (all control mice were dead by day 8). Mice treated intramuscularly with compound 1 exhibited weight gain similar to the uninfected control group at day 11. Mice treated orally with compound 1 exhibited reversible weight loss, and retained greater than 100% of starting weight at day 11.

Example 13

Yellow Fever Virus (YFV) Time Window Golden Hamster Study

Yellow fever virus (Jimenez strain) was injected IP to female Syrian golden hamsters (99 g) at 20 $CCID_{50}$ per hamster (~6.25×$LD_{50}$). Groups were divided as follows: 1) compound 1 was administered beginning −4 h (N=15); 2) compound 1 administered beginning 1 dpi (days post-infection) (N=10); 3) compound 1 administered beginning 2 dpi (N=10); 4) compound 1 administered 3 dpi (N=10); 5) compound 1 administered 4 dpi (N=10); 6) ribavirin administered beginning −4 h (N=10); 7) saline vehicle beginning −4 h (N=16); 8) uninfected hamsters administered compound 1 beginning −4 h (N=3); 9) uninfected hamsters administered saline vehicle beginning −4 h (N=3); and 10) uninfected, untreated normal controls (N=3). Treatment dose was 100 mg/kg IP, BID for 7 days. Study endpoints were morality at 21 days, weight measured on days 0, 3, 5, and 6; serum and liver virus titers (day 4, compound 1 at −4 h, and vehicle at −4 h), and ALT and AST on day 6.

Figure 12:
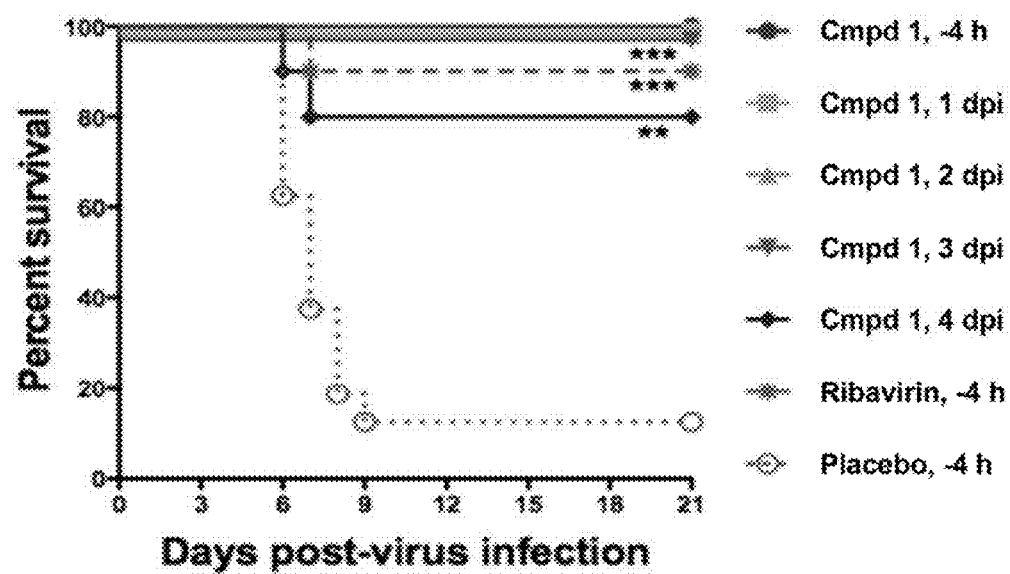
FIG. 12 shows the effect of compound 1 on survival of hamsters infected with Yellow Fever virus.

The study showed enhanced survival for compound 1 with delayed treatment compared to placebo (FIG. 12). Survival of hamsters infected with YFV and treated with compound 1 twice daily for 7 days beginning with various times after virus challenge is indicated (*P<0.001, P<0.1, as compared to placebo). Survival rate was 100% for compound 1 beginning pre-infection, and delayed treatment up to 3 days post-infection. Survival rate was 80% for compound 1 beginning 4 days post-infection, indicating a significant improvement over placebo in groups with delayed treatment. In contrast, ribavrin provided 90% survival beginning pre-infection and the vehicle provided 12.5% survival beginning pre-infection. Most deaths occurred within 10 days of infection. Surviving animals will be re-challenged with YFV at 21 days post-infection.

Figure 13:
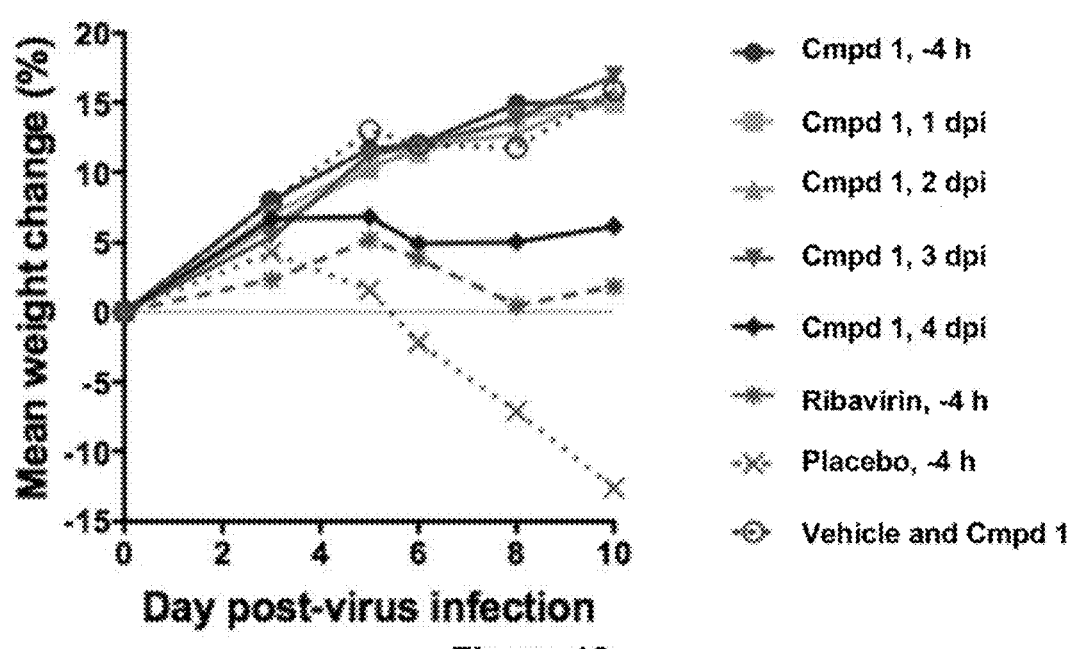
FIG. 13 shows the effect of compound 1 on weight loss in hamsters infected with Yellow Fever virus.

Weight change of hamsters is indicated in FIG. 13. Hamsters infected with YFV and treated with compound 1 from pre-infection to 4 days post-infection showed weight gain over placebo and ribavirin administered pre-infection. Percent weight change of hamsters infected with YFV and treated with compound 1 twice daily for 7 days beginning various times prior to and after virus challenge is shown.

Example 14

Oral Bioavailability of Compound 1 in Rats

Figure 14:
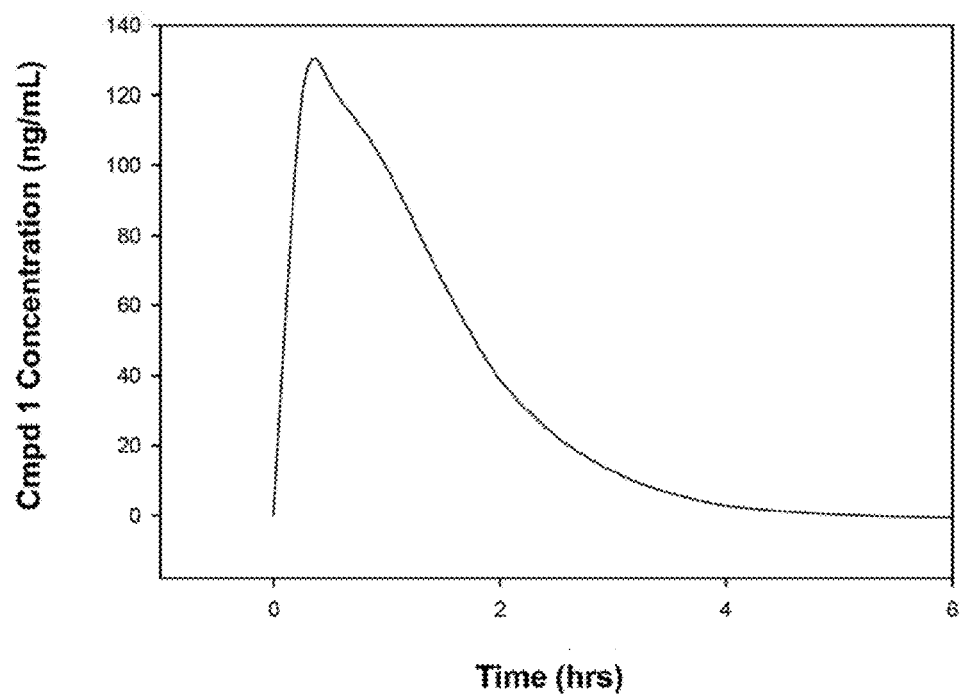
FIG. 14 shows the oral pharmacokinetic curve of compound 1 dosed at 10 mg/kg as measured in rats.

Compound 1 was dosed at 10 mg/kg, PO in rats. The pharmacokinetic curve measuring concentration of compound 1 in rat plasma up to 6 hours is shown in FIG. 14.

Example 15

Marburg Virus Study for Compound 1

Compound 1 was dosed IM in 10-12 week old BALB/c mice challenged (interperitoneally) with 1000 pfu mouse-adapted MARV-Ravn. The study was divided into 10 groups (N=10 per group). Dosing regimens, routes and doses are shown in Table 7. Compound 1 was dissolved in 0.9% saline prior to administration, and health and weight were monitored for 14 days post-infection.

TABLE 7

Study Design for Prophylaxis and Treatment with Compound 1 for Marburg Infection

| Group | N | Treatment | Cmpd 1 Dose (mg/kg) | Cmpd 1 Dose (mg/kg/d) | Route | Regimen* |
|---|---|---|---|---|---|---|
| 1 | 10 | 0.9% saline | — | — | IM | BID; Days 0-8 PI |
| 2 | 10 | Cmpd 1 | 150 | 300 | IM | BID; Days 0-8 PI |
| 3 | 10 | Cmpd 1 | 50 | 100 | IM | BID; Days 0-8 PI |
| 4 | 10 | Cmpd 1 | 15 | 30 | IM | BID; Days 0-8 PI |
| 5 | 10 | Cmpd 1 | 5 | 10 | IM | BID; Days 0-8 PI |
| 6 | 10 | Cmpd 1 | 150 | 300 | IM | BID; +4 h, Days 1-8 PI |
| 7 | 10 | Cmpd 1 | 150 | 300 | IM | BID; Days 1-8 PI |
| 8 | 10 | Cmpd 1 | 150 | 300 | IM | BID; Days 2-8 PI |
| 9 | 10 | Cmpd 1 | 150 | 300 | IM | BID; Days 3-8 PI |
| 10 | 10 | Cmpd 1 | 150 | 300 | IM | BID; Days 4-8 PI |

*Day 0 treatment initiated 4 h prior to infection, except for group 6. Group 6 treatment initiated at 4 h post-infection on day 0.
PI = post-infection Percent survival for the 10 groups in this study to day 12 is included in Table 8. The survival rate for mice treated with vehicle only (0.9% saline) was 60% at day 7 and 30% on days 8-12. Compound 1 was shown to increase survival to at least 90% at day 7, and at least 80% on days 8-12 at all doses.

TABLE 8

Percent Survival Rate for Prophylaxis and Treatment with Compound 1 for Marburg Infection

| Grp | Treatment | Day 0 | Day 1 | Day 2 | Day 3 | Day 4 | Day 5 | Day 6 | Day 7 | Day 8 | Day 9 | Day 10 | Day 11 | Day 12 |
|---|---|---|---|---|---|---|---|---|---|---|---|---|---|---|
| 1 | 0.9% saline | 100 | 100 | 100 | 100 | 100 | 100 | 100 | 60 | 30 | 30 | 30 | 30 | 30 |
| 2 | Cmpd. 1 (150 mg/kg) | 100 | 100 | 100 | 100 | 100 | 100 | 100 | 100 | 100 | 100 | 100 | 100 | 100 |
| 3 | Cmpd. 1 (50 mg/kg) | 100 | 100 | 100 | 100 | 100 | 100 | 100 | 100 | 100 | 100 | 100 | 100 | 100 |
| 4 | Cmpd. 1 (15 mg/kg) | 100 | 100 | 100 | 100 | 100 | 90 | 90 | 90 | 90 | 90 | 90 | 90 | 90 |
| 5 | Cmpd. 1 (5 mg/kg) | 100 | 100 | 100 | 100 | 100 | 100 | 100 | 100 | 100 | 100 | 100 | 100 | 100 |
| 6 | Cmpd. 1 (150 mg/kg) + 4 h | 100 | 100 | 100 | 100 | 100 | 100 | 100 | 100 | 100 | 90 | 90 | 90 | 90 |
| 7 | Cmpd. 1 (150 mg/kg) + 24 h | 100 | 100 | 100 | 90 | 90 | 90 | 90 | 80 | 80 | 80 | 80 | 80 | 80 |
| 8 | Cmpd. 1 (150 mg/kg) + 48 h | 100 | 100 | 100 | 100 | 100 | 100 | 100 | 90 | 90 | 90 | 90 | 90 | 90 |
| 9 | Cmpd. 1 (150 mg/kg) + 72 h | 100 | 100 | 100 | 100 | 90 | 90 | 90 | 90 | 80 | 80 | 80 | 80 | 80 |
| 10 | Cmpd. 1 (150 mg/kg) + 96 h | 100 | 100 | 100 | 100 | 100 | 100 | 100 | 100 | 100 | 90 | 90 | 90 | 90 |

Although the invention has been described and illustrated in the foregoing illustrative embodiments, it is understood that the present disclosure has been made only by way of example, and that numerous changes in the details of implementation of the invention can be made without departing from the spirit and scope of the invention, which is limited only by the claims that follow. Features of the disclosed embodiments can be combined and rearranged in various ways within the scope and spirit of the invention.

What is claimed is:

1. A method of treating a viral infection, comprising administering to a subject in need thereof a therapeutically effective amount of a compound having the following structure:

![structure]

or a pharmaceutically acceptable salt or hydrate thereof; wherein the virus is a member of a virus family selected from the group consisting of orthomyxoviridae, paramyxoviridae, arenaviridae, bunyaviridae, flaviviridae, filoviridae, togaviridae, picornaviridae, poxviridae, adenoviridae, and coronaviridae virus families.

2. The method of claim 1, wherein said subject is a mammal.

3. The method of claim 1, wherein the subject is a human.

4. The method of claim 1, wherein the virus is selected from the group consisting of adenovirus, rhinovirus, polio, measles, Ebola, Coxsackie, small pox, yellow fever, Dengue fever, influenza A, influenza B, lassa, lymphocytic choriomeningitis, junin, machupo, guanarito, hantavirus, Rift Valley Fever, La Crosse, California encephalitis, Crimean-Congo, Marburg, Japanese Encephalitis, Kyasanur Forest, Eastern equine encephalitis, Western equine encephalitis, severe acute respiratory syndrome (SARS), parainfluenza, Tacaribe, vaccinia, and pichinde viruses.

5. The method of claim 1, wherein the virus is selected from the group consisting of Ebola, yellow fever, Marburg, influenza A and influenza B viruses.

6. The method of claim 1, wherein the virus is Ebola virus.

7. The method of claim 6, wherein said subject is a human.

8. The method of claim 1, further comprising co-administering to the subject an effective amount of an anti-viral agent.

9. The method of claim 8, wherein the anti-viral agent is a neuraminidase inhibitor.

10. The method of claim 8, wherein the anti-viral agent is selected from the group consisting of laninamivir, oseltamivir, zanamivir, and peramivir.

11. The method of claim 8, wherein the anti-viral agent is peramivir.

12. The method of claim 1, wherein the compound is administered intravenously, intraperitoneally, intramuscularly, or orally.

13. The method of claim 1, wherein the therapeutically effective amount is delivered in a single dose per day or more than one dose per day.

14. The method of claim 13, wherein the total dose per day is about 5 to about 50 mg/kg, about 50 to about 80 mg/kg, about 80 to about 150 mg/kg, about 250 to about 350 mg/kg, about 350 to about 550 mg/kg, about 450 to about 550 mg/kg, about 550 to about 700 mg/kg, or about 700 to about 100 mg/kg.

15. The method of claim 13, wherein the total dose per day is 10 mg/kg, 30 mg/kg, 100 mg/kg, 150 mg/kg, 250 mg/kg, or 300 mg/kg.

16. A method of suppressing a viral infection, comprising administering to a subject in need thereof a therapeutically effective amount of a compound having the following structure:

![structure]

or a pharmaceutically acceptable salt or hydrate thereof; wherein the virus is a member of a virus family selected from the group consisting of orthomyxoviridae, paramyxoviridae, arenaviridae, bunyaviridae, flaviviridae, filoviridae, togaviridae, picornaviridae, poxviridae, adenoviridae, and coronaviridae virus families.

17. The method of claim 16, wherein said subject is a mammal.

18. The method of claim 16, wherein the subject is a human.

19. The method of claim 16, wherein the virus is selected from the group consisting of adenovirus, rhinovirus, polio, measles, Ebola, Coxsackie, small pox, yellow fever, Dengue fever, influenza A, influenza B, lassa, lymphocytic choriomeningitis, junin, machupo, guanarito, hantavirus, Rift Valley Fever, La Crosse, California encephalitis, Crimean-Congo, Marburg, Japanese Encephalitis, Kyasanur Forest, Eastern equine encephalitis, Western equine encephalitis, severe acute respiratory syndrome (SARS), parainfluenza, Tacaribe, vaccinia, and pichinde viruses.

20. The method of claim 16, wherein the virus is selected from the group consisting of Ebola, yellow fever, Marburg, influenza A and influenza B viruses.

21. The method of claim 16, wherein the virus is Ebola virus.

22. The method of claim 21, wherein said subject is a human.

23. The method of claim 16, further comprising co-administering to the subject an effective amount of an anti-viral agent.

24. The method of claim 23, wherein the anti-viral agent is a neuraminidase inhibitor.

25. The method of claim 23, wherein the anti-viral agent is selected from the group consisting of laninamivir, oseltamivir, zanamivir, and peramivir.

26. The method of claim 23, wherein the anti-viral agent is peramivir.

27. The method of claim 16, wherein the compound is administered intravenously, intraperitoneally, intramuscularly, or orally.

28. The method of claim 16, wherein the therapeutically effective amount is delivered in a single dose per day or more than one dose per day.

29. The method of claim 28, wherein the total dose per day is about 5 to about 50 mg/kg, about 50 to about 80 mg/kg, about 80 to about 150 mg/kg, about 250 to about 350 mg/kg, about 350 to about 550 mg/kg, about 450 to about 550 mg/kg, about 550 to about 700 mg/kg, or about 700 to about 100 mg/kg.

30. The method of claim 28, wherein the total dose per day is 10 mg/kg, 30 mg/kg, 100 mg/kg, 150 mg/kg, 250 mg/kg, or 300 mg/kg.

* * * * *